United States Patent
Leong et al.

(10) Patent No.: US 12,308,092 B2
(45) Date of Patent: May 20, 2025

(54) SYSTEMS AND METHODS FOR THE ANALYSIS OF PROXIMITY BINDING ASSAY DATA

(71) Applicant: LIFE TECHNOLOGIES CORPORATION, Carlsbad, CA (US)

(72) Inventors: Harrison Leong, San Francisco, CA (US); Nivedita Sumi Majumdar, Foster City, CA (US); Elana E Swartzman, Alameda, CA (US)

(73) Assignee: LIFE TECHNOLOGIES CORPORATION, Carlsbad, CA (US)

( * ) Notice: Subject to any disclaimer, the term of this patent is extended or adjusted under 35 U.S.C. 154(b) by 1204 days.

(21) Appl. No.: 15/967,501

(22) Filed: Apr. 30, 2018

(65) Prior Publication Data

US 2018/0330047 A1    Nov. 15, 2018

Related U.S. Application Data

(63) Continuation of application No. 13/885,995, filed as application No. PCT/US2011/061034 on Nov. 16, 2011, now abandoned.

(60) Provisional application No. 61/414,409, filed on Nov. 16, 2010.

(51) Int. Cl.
G16B 20/00    (2019.01)
G16B 40/00    (2019.01)

(52) U.S. Cl.
CPC ............. *G16B 20/00* (2019.02); *G16B 40/00* (2019.02)

(58) Field of Classification Search
CPC .... G01N 2800/60; G01N 33/53; G01N 33/68; C12Q 1/686; C12Q 1/6851; C12Q 1/6876; C12Q 1/6865; C12Q 2531/107; C12Q 2531/143; C12Q 1/6832; C12Q 2527/101; C12Q 2600/158; C12Q 1/6804; C12Q 1/6883; C12Q 2600/156; C12Q 2600/106; C12Q 1/6869; C12Q 1/6841; C12Q 1/6853; C12Q 1/6862; C12Q 1/6818; C12Q 1/682; C12Q 1/6839; C12Q 2525/191; C12Q 2525/197; C12Q 2525/203; C12Q 2525/205; C12Q 2527/125; C12Q 2527/146; C12Q 2527/143; C12Q 2537/165; C12Q 2543/101; C12Q 2545/10; C12Q 2545/113; C12Q 2545/107; C12Q 2549/10; C12Q 2561/125; C12Q 2565/101; C12Q 2565/531; C12Q 2565/543; C12Q 2565/537; C12Q 2565/549; C12Q 2600/136; C12Q 2600/142; C12Q 2600/16; C12Q 2600/166; C12N 2310/3513; G16B 25/20; G16B 20/00; G16B 25/00; G16B 40/00; G16B 25/10; G16B 30/00; G16B 50/00; G16B 15/00; G16B 5/00; G16B 20/20; G16B 15/20; G16B 35/00; G16B 15/30; G16B 20/30; G16B 40/10; G16B 35/20; G16B 50/30; G16B 35/10; G16B 45/00; G16B 50/20; C40B 30/04; C40B 40/10; G16C 20/64

See application file for complete search history.

(56) References Cited

U.S. PATENT DOCUMENTS

| 10,208,335 B2 * | 2/2019 | Chen ...................... G16B 40/00 |
| 11,447,815 B2 * | 9/2022 | Chen ...................... G16B 25/00 |
| 2002/0058262 A1 | 5/2002 | Sagner et al. |
| 2008/0133198 A1 | 6/2008 | Carrick |

FOREIGN PATENT DOCUMENTS

WO    WO-2007117444 A2 * 10/2007 ........... C12N 15/111

OTHER PUBLICATIONS

Forina et al. 2007 Multivariate calibration. Journal of Chromatography A. 1158:61-93. (Year: 2007).*
Goll (2006) Evaluation of absolute quantitation by nonlinear regression in probe-based real-time PCR. BMC Bioinformatics vol. 7: 107, 11 pages. (Year: 2006).*
Yoshida et al. 2009 Antibody-specific aptamer-based PCR analysis for sensitive protein detection. Analytical bioanalytical chemistry vol. 395, p. 1089-1096. (Year: 2009).*
Swartzman (Jan. 2010) Expanding application of protein analysis using proximity ligation and qPCR. Methods 50:S23-S26. (Year: 2010).*
Liao et al (Nov. 2010) Aptamer-based sensitive detection of target molecules via RT-PCR signal amplification. Bioconjugate Chemistry. 21:2183-2189. (Year: 2010).*

(Continued)

*Primary Examiner* — Mary K Zeman
(74) *Attorney, Agent, or Firm* — JONES ROBB, PLLC

(57) ABSTRACT

A proximity binding assay (PBA) is performed on at least one test sample, at least one reference sample, a background sample, and one or more calibration samples using a thermal cycler instrument. Ct values are determined for at least one set of test sample data and at least one set of reference sample data. Background corrected Ct values are calculated using a corresponding value in a background sample data set. A linear range is determined for the background corrected Ct values as a function of sample quantity. A linear regression line is calculated for each linear range. One or more parameter values of an exponential model (EM) fold change formula are estimated from the one or more sets of calibration sample data. A target protein quantity and associated confidence interval are calculated using the linear regression lines and the EM fold change formula.

7 Claims, 16 Drawing Sheets

(56) References Cited

OTHER PUBLICATIONS

Fredriksson 2002 Proximity Ligation: transforming protein analysis into nucleic acid detection through proximity dependent ligation of DNA sequence tagged protein binders. Univeritatis Upsaliensis. 34 pages. (Year: 2002).*
BOSTER online definition of positive and negative controls. Boster.com downloaded May 24, 2023 (Year: 2023).*
Wikipedia definition of negative controls in experimentation, downloaded May 24, 2023 (Year: 2023).*
Lipstitch (2011) Negative controls: a tool for detecting confounding and bias in observational studies. Epidemiology, May 2010, vol. 21, No. 3, p. 383-388. (Year: 2011).*
Fredriksson, S., (2002). Protein detection using proximity-dependent DNA ligation assays. Nat Biotechnol 20(5): 473-477. (Year: 2002).*
Yuan et al., "Statistical analysis of real-time PCR data," BMC bioinformatics, vol. 7, No. 1, 2006, 12 pages.
Chervoneva et al., "Statistical algorithm for assuring similar efficiency in standards and samples for absolute quantification by real-time reverse transcription polymerase chain reaction," Analytical Biochemistry, vol. 348, Issue 2, 2006, pp. 198-208.
International Search Report and Written Opinion issued in International Application No. PCT/US2011/061034 dated May 31, 2012, 9 pages.

* cited by examiner

SYSTEMS AND METHODS FOR THE ANALYSIS OF PROXIMITY BINDING ASSAY DATA

CROSS-REFERENCE TO RELATED APPLICATIONS

This application is a continuation of U.S. application Ser. No. 13/885,995, filed Jul. 29, 2013, which is a 371 of International Application No. PCT/US2011/061034, filed Nov. 16, 2011, which claims the benefit of priority of U.S. Provisional Application No. 61/414,409, filed Nov. 16, 2010 The entire contents of these applications are hereby incorporated herein by reference.

FIELD

The present disclosure generally relates to methods for analyzing proximity binding assay (PBA) data to overcome the shortcomings of traditional methods for quantification using the analysis of amplification data for oligonucleotides.

BACKGROUND

Generally, for numerous types of bioanalysis, the sensitive quantitation of a biomolecule at low levels in a sample is highly desirable for several applications. For example, sensitive quantification is useful to monitor the dynamic expression levels of an intact, post-translationally modified protein in a particular cell or tissue sample or samples. In many cases, the amount of sample of interest, for example, the number of cells or mass of tissue, may be very small. Additionally, the number of copies of the target protein of interest may be very low. In such cases, an assay for the presence of a protein in sub-femtomole concentrations may be needed.

Currently, proximity binding assays as a class of analyses offer the advantages of the sensitivity and specificity of biorecognition binding, along with the exponential signal amplification offered by a variety of oligonucleotide amplification reactions, such as the polymerase chain reaction (PCR).

However, the combination of a binding event, followed by an oligonucleotide amplification reaction event produces data with characteristics requiring specialized analysis methods. Such methods should be readily adapted to the broad class of proximity binding assays, and should provide the user with results presented in readily useful form and format. Accordingly, there is a need in the art for methods for the analysis of proximity binding assay (PBA) data.

SUMMARY

According to various embodiments described herein, a system, method, and computer-readable medium are provided for analyzing proximity binding assay data using calibration data. Analyzing the proximity binding assay data includes calculating a target protein quantity from this data. The system includes a thermal cycler instrument and a processor in communication with the thermal cycler instrument. The method includes steps that use a thermal cycler instrument and a processor.

According to various embodiments, a non-transitory and tangible computer-readable storage medium is encoded with instructions that are executed on a processor. The instructions executed on the processor perform a method for analyzing proximity binding assay data. The method includes providing a system of distinct software modules that includes a measurement module and an analysis module.

In various embodiments, a thermal cycler instrument performs a proximity binding assay on at least one test sample, at least one reference sample, a background sample, and one or more calibration samples. The thermal cycler instrument generates proximity binding assay data. This proximity binding assay data includes at least one set of test sample data, at least one set of reference sample data, a background sample data set, and one or more sets of calibration sample data. A processor receives this data from the thermal cycler instrument. In the computer program product, the processor receives this data using the measurement module.

According to various embodiments, in the system and method, the processor is configured to perform a number of steps. The processor determines cycle threshold (Ct) values for at least one set of test sample data and at least one set of reference sample data. These may include successive dilutions of the sample. The processor calculates background corrected Ct values for each value in the test sample data set and the reference sample data set using a value in the background sample. The processor determines a linear range for the background corrected Ct values as a function of sample dilution. The processor calculates a linear regression line for each linear range that is determined. The processor estimates one or more parameter values of an exponential model (EM) fold change formula from the one or more sets of calibration sample data. Finally, the processor uses the EM fold change formula and regression lines to calculate a relative target protein quantity between the test and reference sample or absolute quantity of the test sample depending on whether the absolute or relative quantity information is available from the reference sample.

In various embodiments, the processor further detects and removes outlier Ct values before determining the linear range for the background corrected Ct values.

In various embodiments, the processor determines the linear range for the background corrected Ct values by calculating a weighted sum. The weighted sum is a sum of the normalized slope, the normalized linearity, and the normalized position for a plurality of the background corrected Ct values. The processor then ranks the plurality of the background corrected Ct values based on the calculated weighted sum. The processor determines the linear range by extending a line in two directions from a background corrected Ct value with the highest ranked weighted sum until a threshold is reached in each direction.

In various embodiments, the processor further calculates a confidence interval for the target protein quantity.

These and other features of the present teachings are set forth herein.

DETAILED DESCRIPTION

To provide a more thorough understanding of the present invention, the following description sets forth numerous specific details, such as specific configurations, parameters, examples, and the like. It should be recognized, however, that such description is not intended as a limitation on the scope of the present invention, but is intended to provide a better description of the exemplary embodiments.

Various embodiments of systems and methods described herein are for analyzing proximity binding assay (PBA) data. As a class, proximity binding assays offer the advantages of the sensitivity and specificity of biorecognition binding, along with the exponential signal amplification offered by a variety of oligonucleotide amplification reactions. Amplification reactions may be, but are not limited to, polymerase chain reaction (PCR). However, unlike the class of oligonucleotide amplification reactions, the class of proximity binding assays has reaction kinetics governed by an additional step of the binding of a biorecognition probe (BRP) with a target molecule, as will be discussed in more detail subsequently. Accordingly, various embodiments of proximity binding assays may require methods for the analysis of PBA data that are particularly suited to the unique characteristics of such data.

Figure 1:
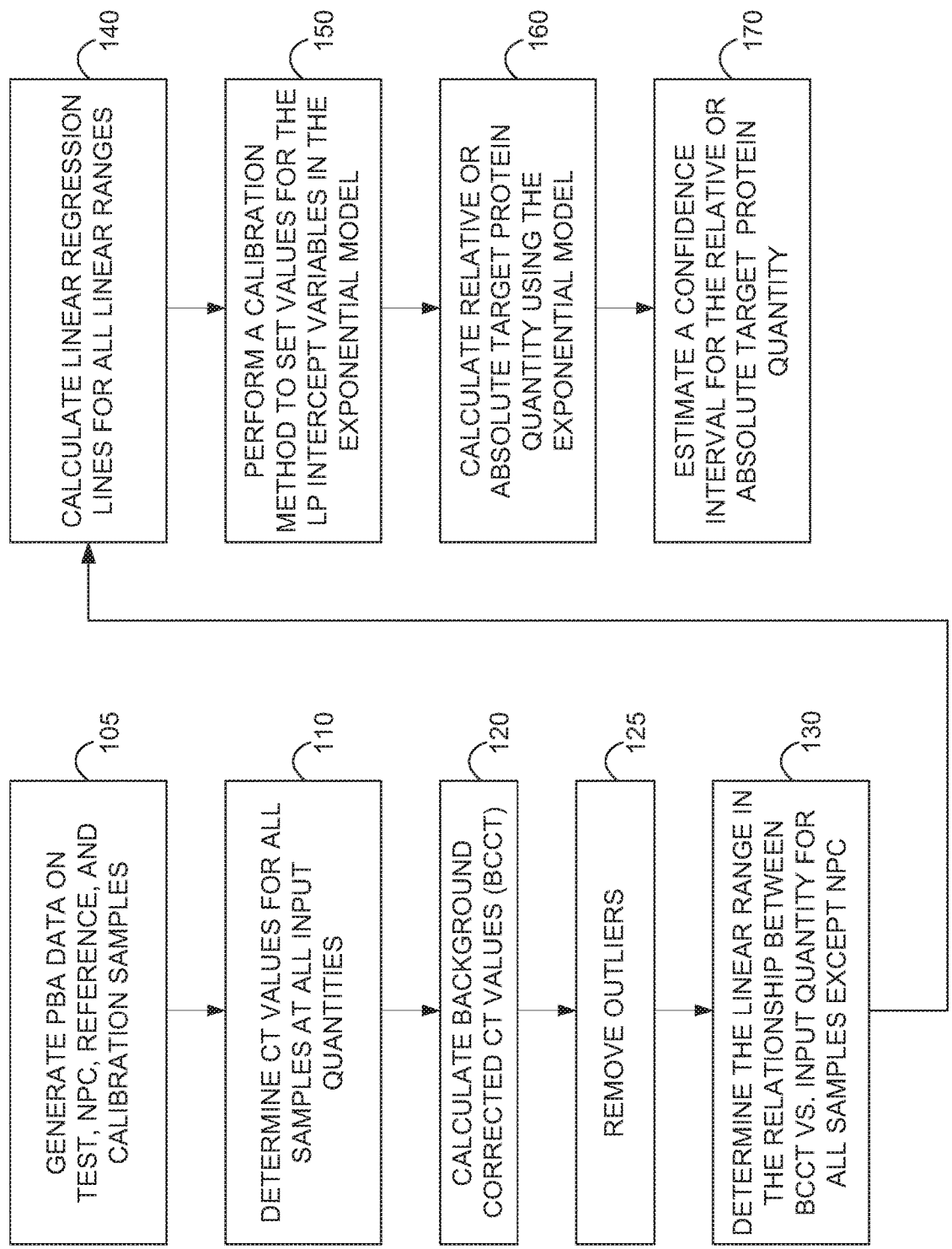
FIG. 1 is a flow chart that depicts various embodiments of methods for the analysis of proximity binding assay (PBA) data.
Figure 2A:
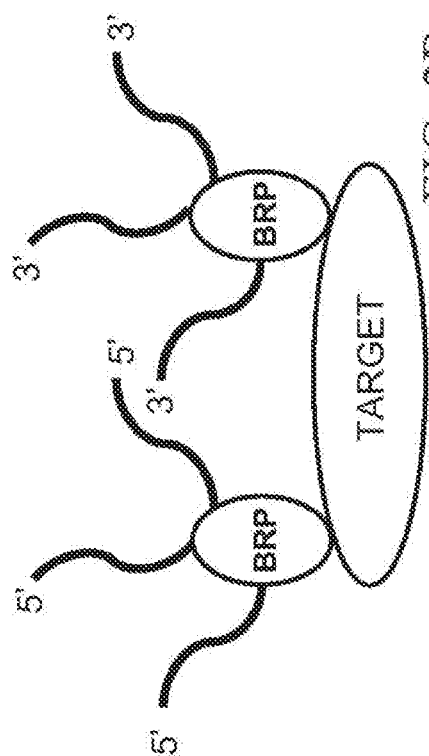
FIGS. 2A-2D depict various embodiments of a proximity binding assay.
Figure 2B:
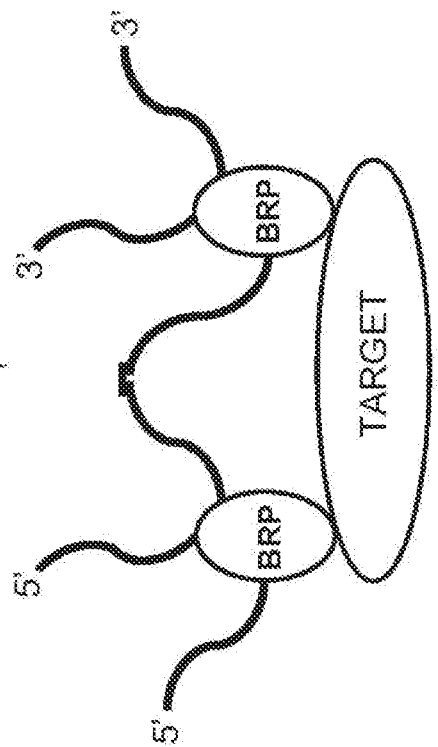
Figure 2C:
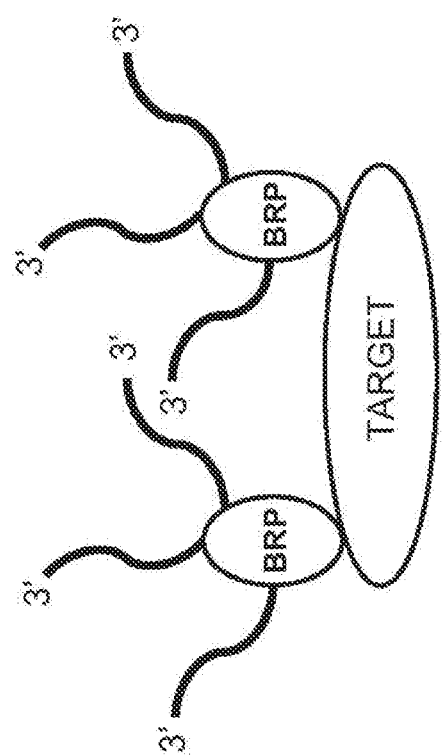

Various embodiments of methods for the analysis of PBA data may be performed using various embodiments of method 100 of FIG. 1. As depicted in FIG. 2A-FIG. 2C, proximity binding assays may be characterized by a biorecognition binding event, as depicted in FIG. 2A, in which a biorecognition probe (BRP) binds to a target biomolecule. For bioanalysis, examples of biorecognition binding may include, but are not limited by oligonucleotide-oligonucleotide, protein-protein, ligand-receptor, antigen-antibody, lectin-polysaccharide, aptamer-protein, enzyme-substrate, and cofactor-protein. According to various embodiments of proximity binding assays, a BRP may enable signal amplification in order to provide for the detection of the target molecule.

Figure 2D:
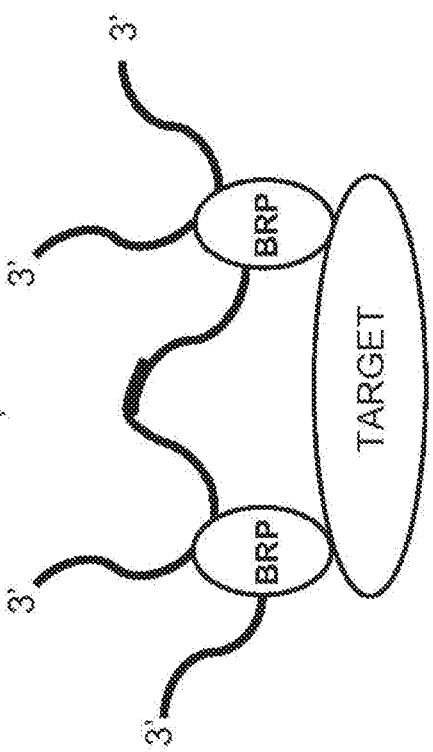

In FIG. 2A-FIG. 2D, various embodiments of BRPs modified with oligonucleotide sequences are shown. According to various embodiments, as shown in FIG. 2A, BRPs may be prepared so that strands in proximity to one another after the binding of the BRPs to a target are of opposite orientation. For various embodiments of BRPs, as shown in FIG. 2B, one population of BRP may have 3' strands of an oligonucleotide sequence coupled to it, while a second population of BRP may have 5' strands of an oligonucleotide sequences coupled to it, so that the strands in proximity to one another after binding are of the same orientation. For various embodiments of a PBA as shown in FIG. 2A, the BRPs may be designed so that at least the free distal end sequences are complementary, so that the binding of complementary sequences produces a target for extension, as shown in FIG. 2C. For various embodiments of proximity binding assays, with the addition of a splint oligonucleotide in the presence of a ligase enzyme, the proximal 3' and 5' ends may be ligated, as shown in FIG. 2D, forming a target for ligation. For either example, as depicted in FIG. 2C and FIG. 2D, after a target for amplification is formed, and with the addition of amplification reaction components, followed by thermocycling in a thermal cycling system, sequence detection data may be generated. Other methods for detecting oligonucleotides brought into proximity for various embodiments of proximity binding assays include, for example, but not limited by, restriction digestion, and polymerase extension.

According to various embodiments, the term "amplifying", "amplification" and related terms may refer to any process that increases the amount of a desired nucleic acid. Any of a variety of known amplification procedures may be employed in the present teachings, including PCR (see for example U.S. Pat. No. 4,683,202), as well as any of a variety of ligation-mediated approaches, including LDR and LCR (see for example U.S. Pat. Nos. 5,494,810, 5,830,711, 6,054, 564). Some other amplification procedures include isothermal approaches such as rolling circle amplification and helicase-dependent amplification. One of skill in art will readily appreciate a variety of possible amplification procedures applicable in the context of the present teachings. For example, in some embodiments, the amplification may comprise a PCR comprising a real-time detection, using for example a labeling probe.

The term "labeling probe" generally, according to various embodiments, refers to a molecule used in an amplification reaction, typically for quantitative or real-time PCR analysis, as well as end-point analysis. Such labeling probes may be used to monitor the amplification of the target polynucleotide. In some embodiments, oligonucleotide probes present in an amplification reaction are suitable for monitoring the amount of amplicon(s) produced as a function of time. Such oligonucleotide probes include, but are not limited to, the 5'-exonuclease assay TaqMan® probes described herein (see also U.S. Pat. No. 5,538,848), various stem-loop molecular beacons (see e.g., U.S. Pat. Nos. 6,103,476 and 5,925,517 and Tyagi and Kramer, 1996, Nature Biotechnology 14:303-308), stemless or linear beacons (see, e.g., WO 99/21881), PNA Molecular Beacons™ (see, e.g., U.S. Pat. Nos. 6,355, 421 and 6,593,091), linear PNA beacons (see, e.g., Kubista et al., 2001, SPIE 4264:53-58), non-FRET probes (see, e.g., U.S. Pat. No. 6,150,097), Sunrise®/Amplifluor® probes (U.S. Pat. No. 6,548,250), stem-loop and duplex Scorpion™ probes (Solinas et al., 2001, Nucleic Acids Research 29:E96 and U.S. Pat. No. 6,589,743), bulge loop probes (U.S. Pat. No. 6,590,091), pseudo knot probes (U.S. Pat. No. 6,589,250), cyclicons (U.S. Pat. No. 6,383,752), MGB Eclipse™ probe (Epoch Biosciences), hairpin probes (U.S. Pat. No. 6,596,490), peptide nucleic acid (PNA) light-up probes, self-assembled nanoparticle probes, and ferrocene-modified probes described, for example, in U.S. Pat. No. 6,485,901; Mhlanga et al., 2001, Methods 25:463-471; Whitcombe et al., 1999, Nature Biotechnology. 17:804-807; Isacsson et al., 2000, Molecular Cell Probes. 14:321-328; Svanvik et al., 2000, Anal Biochem. 281:26-35; Wolffs et al., 2001, Biotechniques 766:769-771; Tsourkas et al., 2002, Nucleic Acids Research. 30:4208-4215; Riccelli et al., 2002, Nucleic Acids Research 30:4088-4093; Zhang et al., 2002 Shanghai. 34:329-332; Maxwell et al., 2002, J. Am. Chem. Soc. 124:9606-9612; Broude et al., 2002, Trends Biotechnol. 20:249-56; Huang et al., 2002, Chem Res. Toxicol. 15:118-126; and Yu et al., 2001, J. Am. Chem. Soc 14:11155-11161. Labeling probes can also comprise black hole quenchers (Biosearch), Iowa Black (IDT), QSY quencher (Molecular Probes), and Dabsyl and Dabcel sulfonate/carboxylate Quenchers (Epoch). Labeling probes can also comprise two probes, wherein for example a fluorophore is on one probe, and a quencher on the other, wherein hybridization of the two probes together on a target quenches the signal, or wherein hybridization on target alters the signal signature via a change in fluorescence. Labeling probes can also comprise sulfonate derivatives of fluorescenin dyes with a sulfonic acid group instead of the carboxylate group, phosphoramidite forms of fluorescein, phosphoramidite forms of CY 5 (available for example from Amersham). In some embodiments, intercalating labels are used such as ethidium bromide, SYBR® Green I (Molecular Probes), and PicoGreen® (Molecular Probes), thereby allowing visualization in real-time, or end point, of an amplification product in the absence of a labeling probe.

According to various embodiments of proximity binding assays, the target may be a protein. For various embodiments of a proximity binding assay for proteins, a BRP may be directed to a polypeptide primary, secondary, or tertiary structure, such as an aptamer or antibody, or may be directed to a group such as any of a variety of chemical resulting from the in vivo or in vitro modification of a polypeptide structure.

Figure 3:
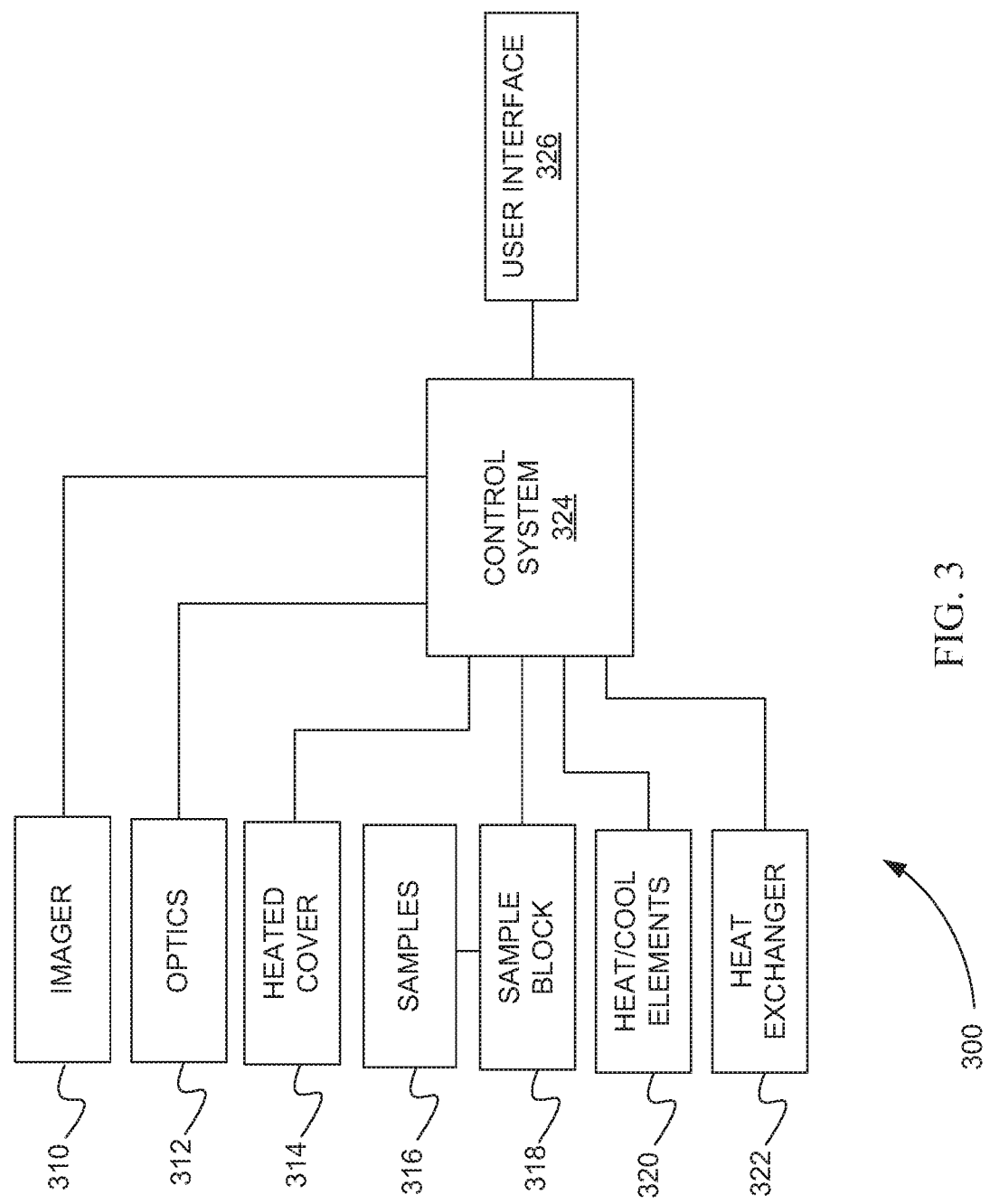
FIG. 3 depicts an exemplary apparatus for generating PBA data according to various embodiments described herein.

According to various embodiments of a thermal cycler instrument 300, as shown in FIG. 3, a thermal cycling instrument may include a heated cover 314 that is placed over a plurality of samples 316 contained in a sample support device. In various embodiments, a sample support device may be a glass, plastic, composite, metal, or any other suitable substrate material having a plurality of sample regions, which sample regions may have a cover between the sample regions and heated cover 314. Some examples of a sample support device may include, but are not limited by, sample tubes or vials, a multi-well plate, such as a standard microtiter plate (i.e. for example, but not limited by, a 96-well, a 384-well plate, 1536-well plate, etc), a microcard, or a substantially planar support, such as a glass or plastic slide, which may or may not be coated or capable of providing current to a sample located thereon. The sample regions in various embodiments of a sample support device may include depressions, indentations, ridges, and combinations thereof, patterned in regular or irregular arrays formed on the surface of the substrate. Various embodiments of a thermal cycler instrument 300 may include a thermal block assembly, which may include a sample block 318, as well as elements for heating and cooling 320, and a heat exchanger 322. In some embodiments, a thermocycler instrument may include temperature blocks which may be at the same or different temperatures and wherein a capillary, tube, channel, or other conduit may be located in the thermocycler, so that a sample may flow through the different temperature blocks as opposed to remaining stationary.

Figure 4:
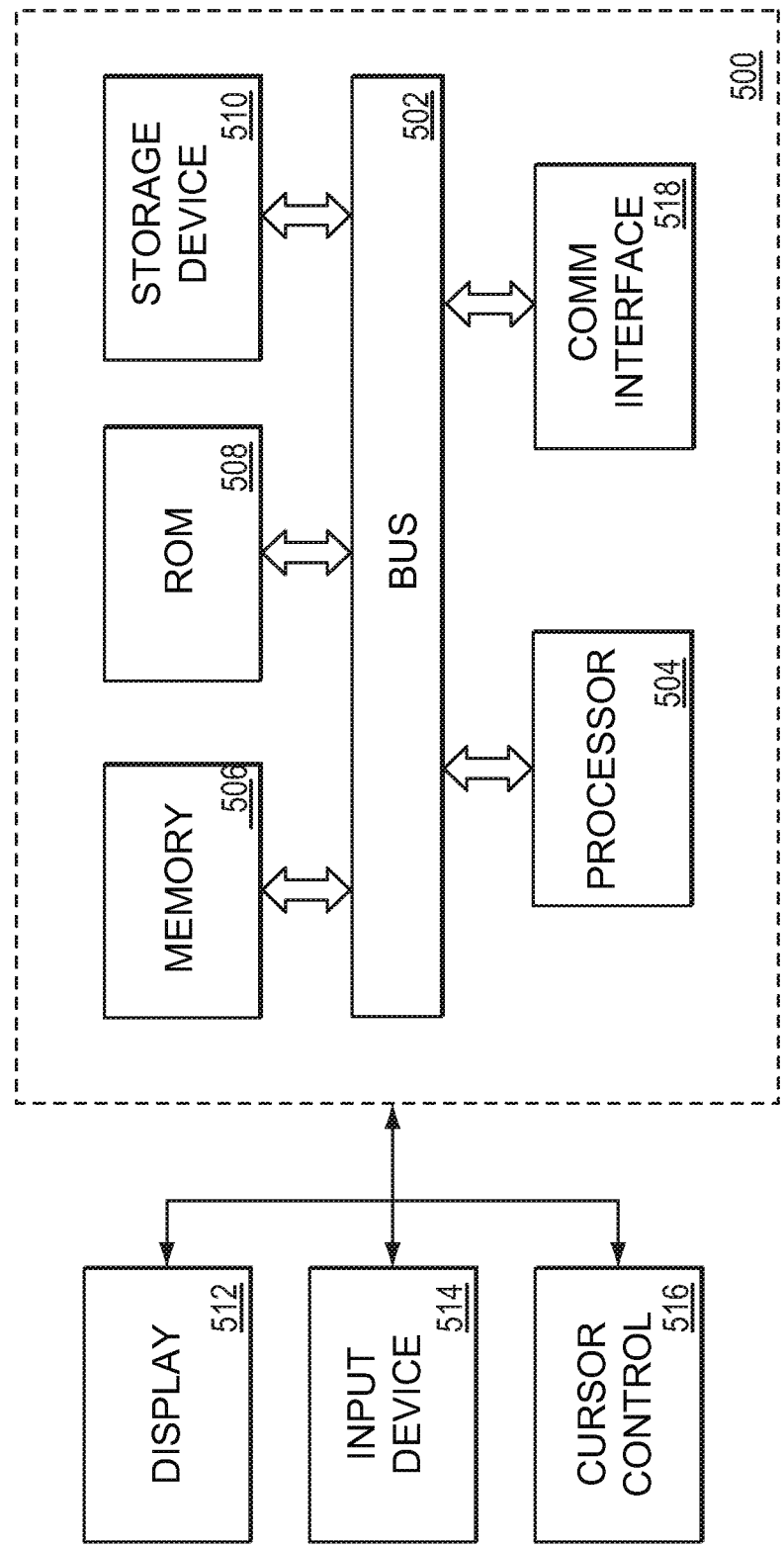
FIG. 4 is an exemplary block diagram that illustrates a computer system according to various embodiments upon which embodiments of methods for the analysis of PBA data may be implemented.

Additionally, various embodiments of a thermal cycling system 300 may have a detection system. A detection system may have an illumination source that emits electromagnetic energy (not shown), a detector or imager 310, for receiving electromagnetic energy from samples 316 in sample support device, and optics 312, which may be located between the illumination source and detector or imager 310. For various embodiments of a thermal cycler instrument 300, a control system 324 may be used to control, for example, but not limited by, the functions of the detection, heated cover, and thermal block assembly. The control system 324 may be accessible to an end user through user interface 326 of a thermal cycler instrument 300. In addition to a user interface system 326, a computer system 500, as depicted in FIG. 4 may serve as to provide control of various functions of a thermal cycler instrument. Additionally, computer system 500 may provide data processing, display and report preparation functions. All such instrument control functions may be dedicated locally to the thermal cycler instrument, or computer system 500 may provide remote control of part or all of the control, analysis, and reporting functions, as will be discussed in more detail subsequently.

Those skilled in the art will recognize that the operations of the various embodiments may be implemented using hardware, software, firmware, or combinations thereof, as appropriate. For example, some processes can be carried out using processors or other digital circuitry under the control of software, firmware, or hard-wired logic. (The term "logic" herein refers to fixed hardware, programmable logic and/or an appropriate combination thereof, as would be recognized by one skilled in the art to carry out the recited functions.) Software and firmware can be stored on computer-readable media. Some other processes can be implemented using analog circuitry, as is well known to one of ordinary skill in the art. Additionally, memory or other storage, as well as communication components, may be employed in embodiments of the invention.

FIG. 4 is a block diagram that illustrates a computer system 500 that may be employed to carry out processing functionality, according to various embodiments, upon which embodiments of a thermal cycler system 300 of FIG. 3 may utilize. Computing system 500 can include one or more processors, such as a processor 504. Processor 504 can be implemented using a general or special purpose processing engine such as, for example, a microprocessor, controller or other control logic. In this example, processor 504 is connected to a bus 502 or other communication medium.

Further, it should be appreciated that a computing system 500 of FIG. 4 may be embodied in any of a number of forms, such as a rack-mounted computer, mainframe, supercomputer, server, client, a desktop computer, a laptop computer, a tablet computer, hand-held computing device (e.g., PDA, cell phone, smart phone, palmtop, etc.), cluster grid, netbook, embedded systems, or any other type of special or general purpose computing device as may be desirable or appropriate for a given application or environment. Additionally, a computing system 500 can include a conventional network system including a client/server environment and one or more database servers, or integration with LIS/LIMS infrastructure. A number of conventional network systems, including a local area network (LAN) or a wide area network (WAN), and including wireless and/or wired components, are known in the art. Additionally, client/server environments, database servers, and networks are well documented in the art.

Computing system 500 may include bus 502 or other communication mechanism for communicating information, and processor 504 coupled with bus 502 for processing information.

Computing system 500 also includes a memory 506, which can be a random access memory (RAM) or other dynamic memory, coupled to bus 502 for storing instructions to be executed by processor 504. Memory 506 also may be used for storing temporary variables or other intermediate information during execution of instructions to be executed by processor 504. Computing system 500 further includes a read only memory (ROM) 508 or other static storage device coupled to bus 502 for storing static information and instructions for processor 504.

Computing system 500 may also include a storage device 510, such as a magnetic disk, optical disk, or solid state drive (SSD) is provided and coupled to bus 502 for storing information and instructions. Storage device 510 may include a media drive and a removable storage interface. A media drive may include a drive or other mechanism to support fixed or removable storage media, such as a hard disk drive, a floppy disk drive, a magnetic tape drive, an optical disk drive, a CD or DVD drive (R or RW), flash drive, or other removable or fixed media drive. As these examples illustrate, the storage media may include a computer-readable storage medium having stored therein particular computer software, instructions, or data.

In alternative embodiments, storage device 510 may include other similar instrumentalities for allowing computer programs or other instructions or data to be loaded into computing system 500. Such instrumentalities may include, for example, a removable storage unit and an interface, such as a program cartridge and cartridge interface, a removable memory (for example, a flash memory or other removable memory module) and memory slot, and other removable storage units and interfaces that allow software and data to be transferred from the storage device 510 to computing system 500.

Computing system 500 can also include a communications interface 518. Communications interface 518 can be used to allow software and data to be transferred between computing system 500 and external devices. Examples of communications interface 518 can include a modem, a network interface (such as an Ethernet or other NIC card), a communications port (such as for example, a USB port, a RS-232C serial port), a PCMCIA slot and card, Bluetooth, etc. Software and data transferred via communications interface 518 are in the form of signals which can be electronic, electromagnetic, optical or other signals capable of being received by communications interface 518. These signals may be transmitted and received by communications interface 518 via a channel such as a wireless medium, wire or cable, fiber optics, or other communications medium. Some examples of a channel include a phone line, a cellular phone link, an RF link, a network interface, a local or wide area network, and other communications channels.

Computing system 500 may be coupled via bus 502 to a display 512, such as a cathode ray tube (CRT) or liquid crystal display (LCD), for displaying information to a computer user. An input device 514, including alphanumeric and other keys, is coupled to bus 502 for communicating information and command selections to processor 504, for example. An input device may also be a display, such as an LCD display, configured with touchscreen input capabilities. Another type of user input device is cursor control 516, such as a mouse, a trackball or cursor direction keys for communicating direction information and command selections to processor 504 and for controlling cursor movement on display 512. This input device typically has two degrees of freedom in two axes, a first axis (e.g., x) and a second axis (e.g., y), that allows the device to specify positions in a plane. A computing system 500 provides data processing and provides a level of confidence for such data. Consistent with certain implementations of embodiments of the present teachings, data processing and confidence values are provided by computing system 500 in response to processor 504 executing one or more sequences of one or more instructions contained in memory 506. Such instructions may be read into memory 506 from another computer-readable medium, such as storage device 510. Execution of the sequences of instructions contained in memory 506 causes processor 504 to perform the process states described herein. Alternatively hard-wired circuitry may be used in place of or in combination with software instructions to implement embodiments of the present teachings. Thus implementations of embodiments of the present teachings are not limited to any specific combination of hardware circuitry and software.

The term "computer-readable medium" and "computer program product" as used herein generally refers to any media that is involved in providing one or more sequences or one or more instructions to processor 504 for execution. Such instructions, generally referred to as "computer program code" (which may be grouped in the form of computer programs or other groupings), when executed, enable the computing system 500 to perform features or functions of embodiments of the present invention. These and other forms of computer-readable media may take many forms, including but not limited to, non-volatile media, volatile media, and transmission media. Non-volatile media includes, for example, solid state, optical or magnetic disks, such as storage device 510. Volatile media includes dynamic memory, such as memory 506. Transmission media includes coaxial cables, copper wire, and fiber optics, including the wires that comprise bus 502.

Common forms of computer-readable media include, for example, a floppy disk, a flexible disk, hard disk, magnetic tape, or any other magnetic medium, a CD-ROM, any other optical medium, punch cards, paper tape, any other physical medium with patterns of holes, a RAM, PROM, and EPROM, a FLASH-EPROM, any other memory chip or cartridge, a carrier wave as described hereinafter, or any other medium from which a computer can read.

Various forms of computer readable media may be involved in carrying one or more sequences of one or more instructions to processor 504 for execution. For example, the instructions may initially be carried on magnetic disk of a remote computer. The remote computer can load the instructions into its dynamic memory and send the instructions over a telephone line using a modem. A modem local to computing system 500 can receive the data on the telephone line and use an infra-red transmitter to convert the data to an infra-red signal. An infra-red detector coupled to bus 502 can receive the data carried in the infra-red signal and place the data on bus 502. Bus 502 carries the data to memory 506, from which processor 504 retrieves and executes the instructions. The instructions received by memory 506 may optionally be stored on storage device 510 either before or after execution by processor 504.

It will be appreciated that, for clarity purposes, the above description has described embodiments of the invention with reference to different functional units and processors. However, it will be apparent that any suitable distribution of functionality between different functional units, processors or domains may be used without detracting from the invention. For example, functionality illustrated to be performed by separate processors or controllers may be performed by the same processor or controller. Hence, references to specific functional units are only to be seen as references to suitable means for providing the described functionality, rather than indicative of a strict logical or physical structure or organization.

In various embodiments of step 105 of method 100 of FIG. 1, for various embodiments of PBA data for protein analysis, test, reference and non-protein control (NPC) samples may be run, and the data may be collected and analyzed using computer system 500. For example, according to various embodiments of a proximity binding assay, an end user may wish to assess the up or down regulation of a protein or proteins in a cell line. For various embodiments of such assays, test samples of a cell line subjected to various conditions may be run. For various embodiments of bioanalyses assessing the up or down regulation of a protein or proteins in a cell line, the determination may be relative quantitation (RQ), in which a reference may be a cell line control that has a target protein or proteins in a defined state. For various embodiments of bioanalyses assessing the up or down regulation of a protein or proteins in a cell line, the determination may be absolute quantification, in which a reference is a set of samples for which target proteins are of a known quantity.

For various embodiments of proximity binding assays utilizing ligated amplicons, as shown for FIG. 2, there is a finite probability that amplicon formation may occur in the absence of target, thereby creating background signal. Additionally, for various embodiments of BRPs, binding may be influenced by variables in a reaction matrix. For example, antigen-antibody binding is known to be influenced by such matrix effects. For at least these reasons, for various embodiments of methods for the analysis of PBA data, as indicated in step 105 of method 100 of FIG. 1, an NPC may be run, in which a target molecule is absent, and the control is designed to compensate for background and matrix effects. According to various embodiments of method 100, the protocols for generating data for test, reference, and NPC samples are not constrained with respect to the manner in which the data may be generated. For example, but not limited by, for various embodiments, samples as indicated in step 105 of method 100 may be run in the same run on the same instrument on the same day, while for other embodiments of method 100, test, reference, and NPC samples may be run on different days and/or on different instruments.

According to various embodiments of methods for the analysis of PBA data, as depicted in step 110 of method 100 of FIG. 1, the determination of threshold cycle or Ct values for all samples at all input quantities may be done. As one of ordinary skill in the art is apprised, the Ct is the cycle number for an oligonucleotide amplification reaction at which the fluorescence generated for a sample exceeds a defined threshold. The threshold cycle, then, is defined as the cycle number of an oligonucleotide amplification reaction at which a sufficient number of amplicons have accumulated to provide for analytical detection above noise. According to various embodiments of step 110 of method 100, a variety of approaches may be taken to determine a Ct value. For example, U.S. Pat. No. 7,228,237 to Woo et al, discloses various embodiments for automatic threshold setting for oligonucleotide amplification reactions, and is incorporated herein by reference in its entirety.

Figure 5:
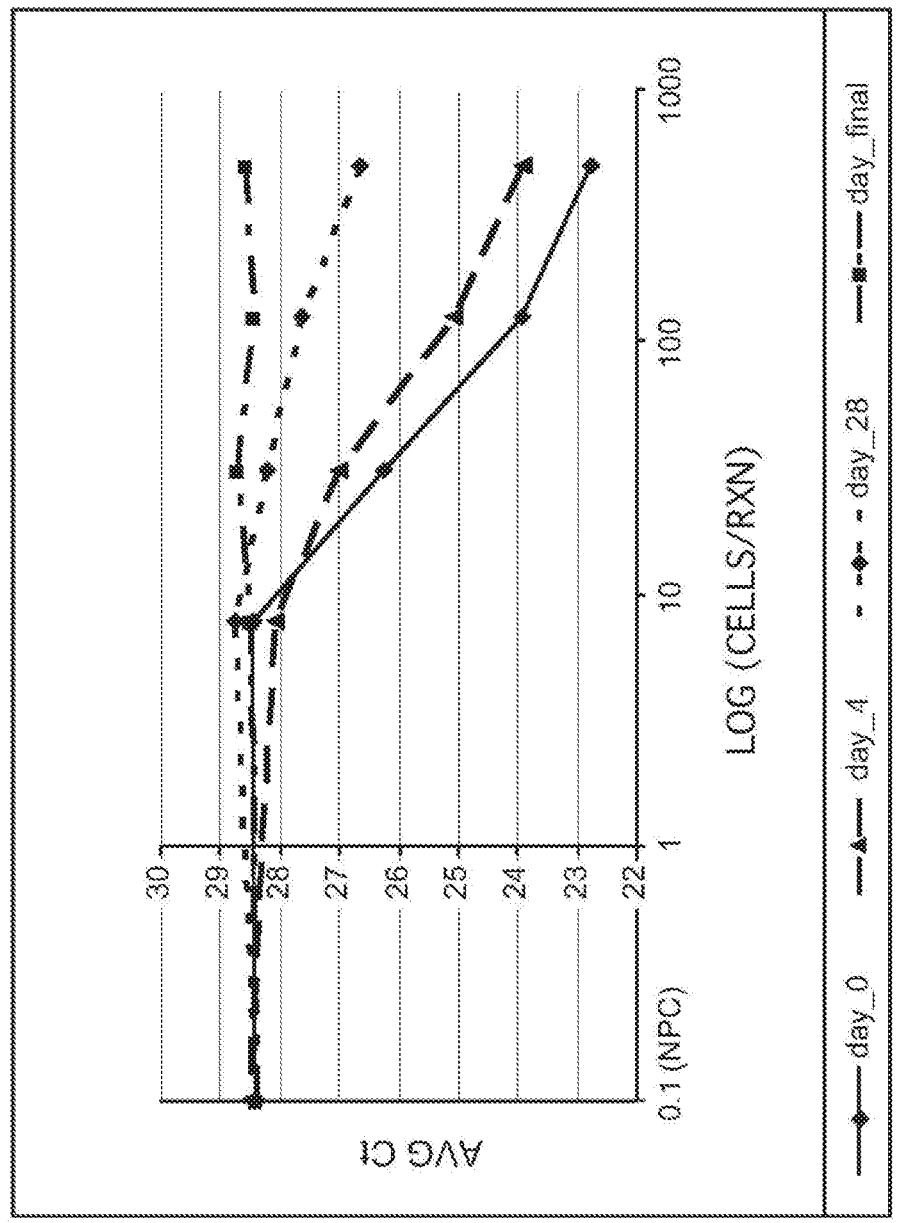
FIG. 5 depicts exemplary graphs of Ct values as a function of log of quantity of test sample for an exemplary proximity binding assay according to various embodiments described herein.
Figure 6:
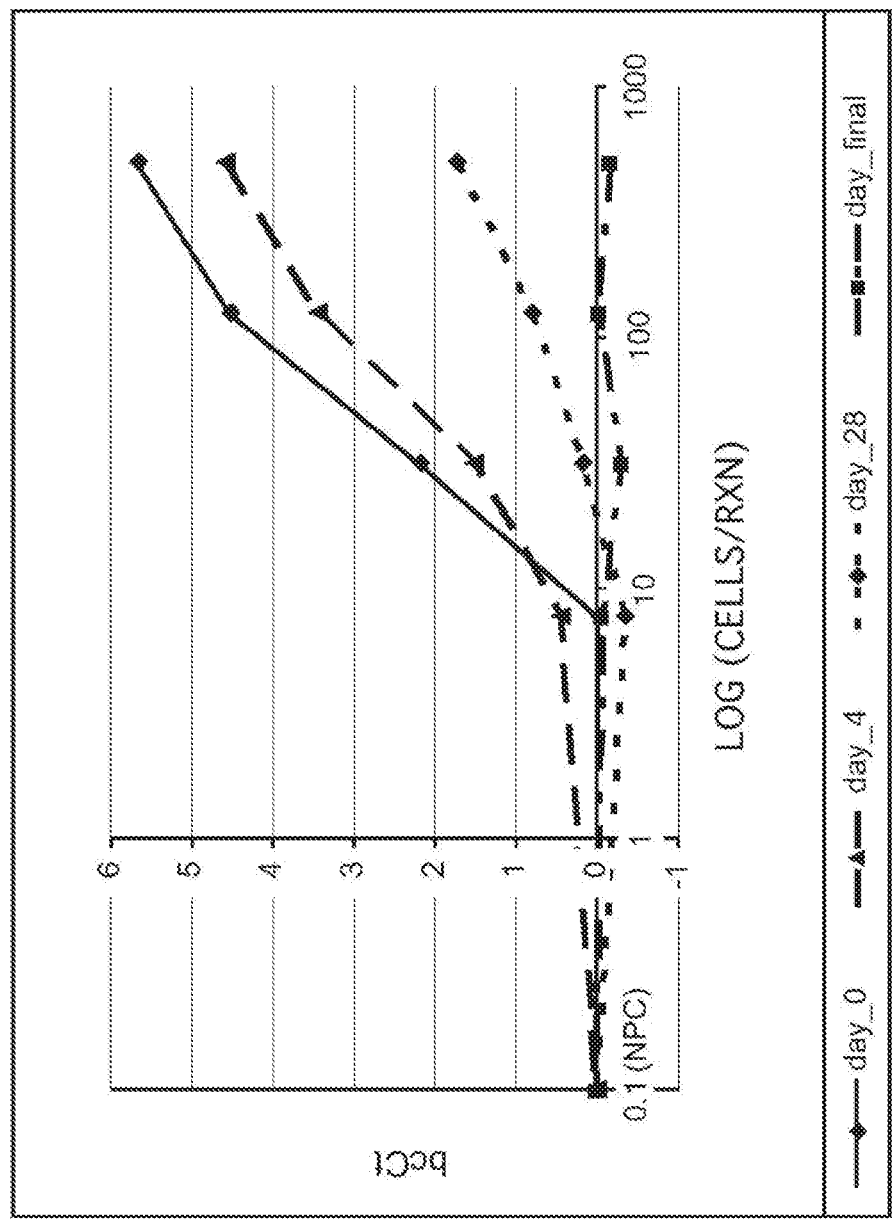
FIG. 6 depicts the exemplary graphs of FIG. 5 that have been corrected for background according to various embodiments of methods for the analysis of PBA data.

In FIG. 5, a plot of the Ct values as a function of sample quantity for PBA data generated for the analysis of the protein OCT3/4 in a NTERA-2 cell line is shown. According to various embodiments, a sample quantity may be, for example but not limited by, the number of cells or the concentration of a biomolecule. For each graph shown in FIG. 5, each point represents a serial dilution of an NTERA-2 cell sample taken for analysis. As previously mentioned, for various embodiments of methods for the analysis of PBA data, a proximity binding assay is an assay in which oligonucleotide-labeled BRP is a monoclonal or polyclonal antibody. This is shown in FIG. 2. The exemplary PBA data shown in FIG. 2 was generated with an embodiment of a proximity binding assay utilizing an antibody-based BRP and qPCR analysis using TAQMAN® PCR reagents In various embodiments of methods for the analysis of PBA data, as indicated in step 120 of method 100 of FIG. 1, the average Ct value for the NPC samples or background samples associated with a particular set of samples may be subtracted from the average Ct values for each data point in the dilution series for each sample. An example of the background corrected Ct (bcCt) or delta Ct (ΔCt) values for each data point for each curve for the OCT3/4 protein in the NTERA-2 cells is shown in FIG. 6. As one of ordinary skill in the art of oligonucleotide analysis by PCR would know, the graphs for the data presented are normally of parallel orientation for the linear phase of an amplification reaction. As can be seen in FIG. 6, the PBA data for this exemplary analysis of OCT3/4 in NTERA cells is atypical of such amplification data, since the linear phases of the curves are not parallel. In that regard, various embodiments of analysis of PBA data specifically address the atypical nature of data generated for such analyses.

Figure 7:
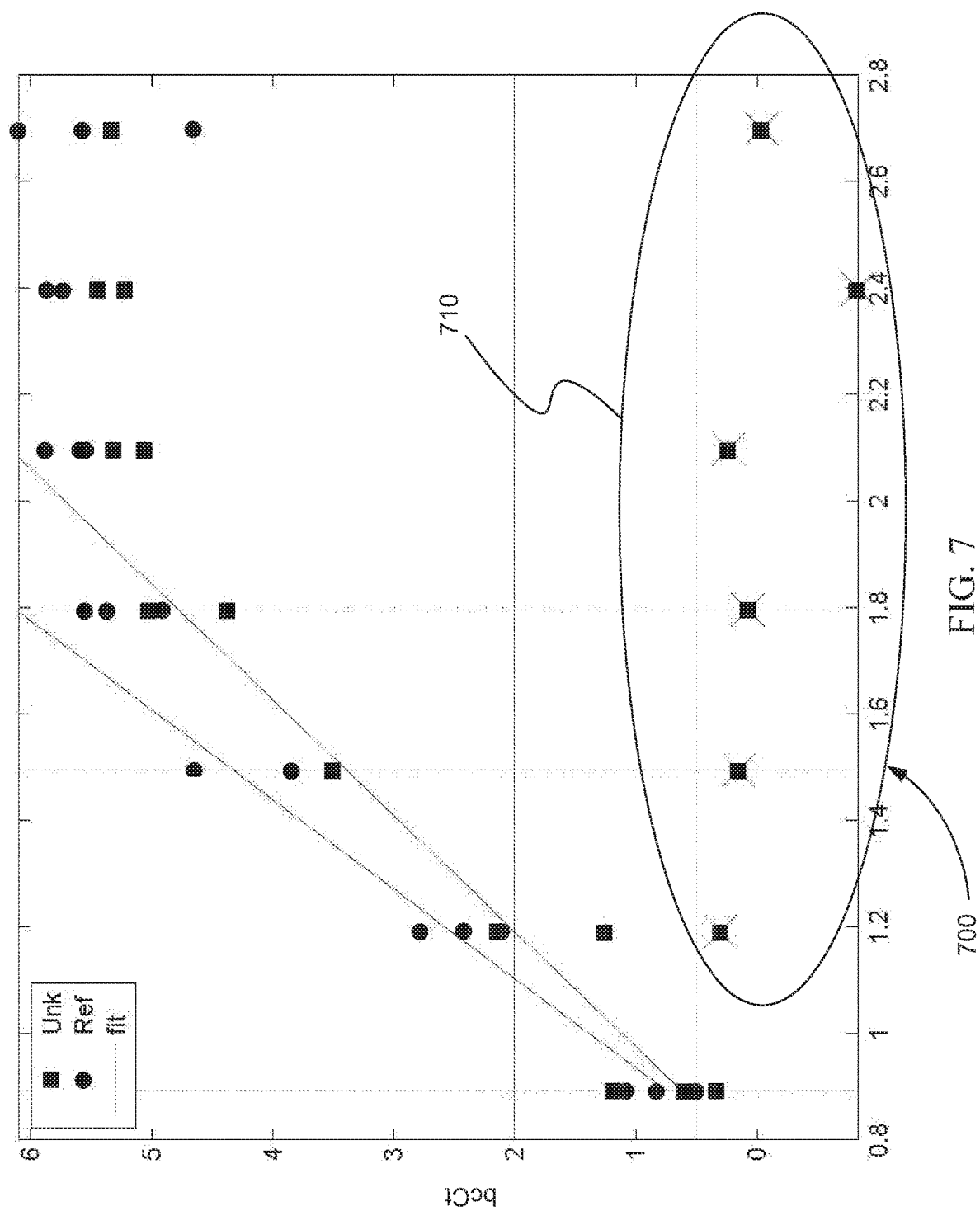
FIG. 7 depicts exemplary graphs of Ct values including detected outliers according to various embodiments for detecting outliers.

In various embodiments of methods for the analysis of PBA data, as indicated in step 125 of method 100 of FIG. 1, a data point is flagged as an outlier if it deviates from its replicate group median by more than N standard deviations. N is specified by a user and a standard deviation may be estimated using data for one dilution or across all dilutions, for example. In various embodiments, N is set through an outlier sensitivity control. Outlier detection is applied to each replicate group of bcCt values. Additional outlier detection methods may be applied, for example, for cases where there are replicate data points above and below a bcCt threshold (0.5 for example), the points in the minority (either the points above or the points below the threshold) are considered outliers if they differ from the median of the majority group by more than N standard deviations. The standard deviation is based on the majority groups (each dilution has a majority group but may not have a minority group). If there is a tie, for example, no outlier is called. An example of outlier detection using this additional detection method applied to a group of bcCt values is shown in plot 700 of FIG. 7. Data points 710 are detected as outliers in plot 700.

According to various embodiments of methods for the analysis of PBA data, as indicated in step 130 of method 100 of FIG. 1, the linear range of the relationship between the bcCt values and the input quantity is determined for all samples except NPC. The underlying structure of the PBA data is roughly a sigmoid function rising from left to right in a bcCt vs. log(input quantity) plot, where input quantity increases from left to right. One goal is to determine the maximum and minimum log(input quantity) values (x values) such that, between these x values, there is a linear relationship between bcCt and log(input quantity). All points with the same x value are considered to be in a replicate group.

Figure 8:
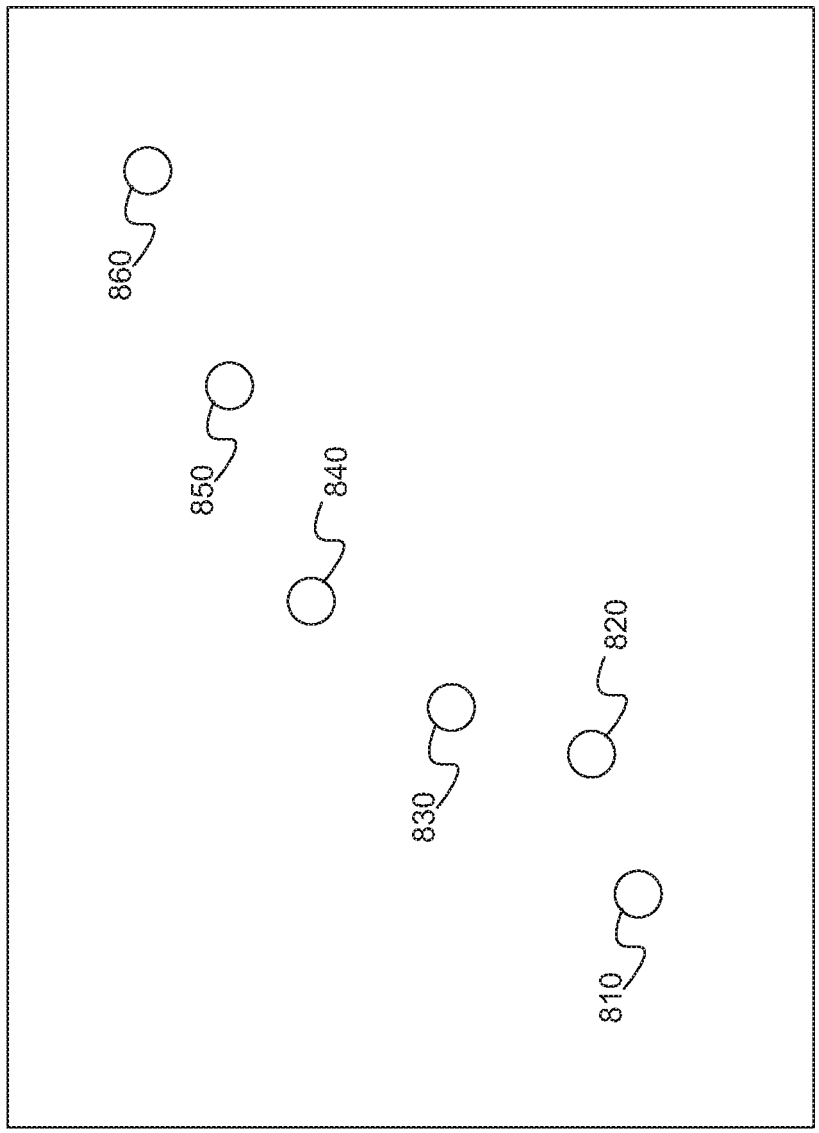
FIG. 8 depicts exemplary graphs of Ct values as a function of log of quantity that are assessed to determine a linear range.

According to various embodiments of methods for the analysis of PBA data, the linear range of the relationship between the bcCt values and the log (input quantity) is determined by assessing each data point or each group of data points based on slope, linearity, and position. In plot 800 of FIG. 8, bcCt values 810-860 are plotted as a function of log (input quantity). By assessing each of bcCt values 810-860 based on slope, linearity, and position, bcCt values 820 and 830 are chosen over 840 and 850 for the linear range, for example.

In various embodiments, bcCt values 810-860 are median bcCt values calculated at each input quantity where data is available. Not all median bcCt values may be assessed for the linear range. For example, only median bcCt values above a criterion threshold may be assessed. An exemplary criterion threshold can include, but is not limited to, the noise level or a level below which a thermal cycler instrument cannot record a Ct value. Assuming bcCt values 810-860 are above the criterion threshold, each value is assigned a measure of slope, linearity, and position. The slope for each value is calculated for a line extended to one or more adjacent values, for example. The linearity for each value is calculated by fitting a line to the value and two or more adjacent values, for example. The position for each value is the x position, for example. The measures of slope, linearity, and position for each value are normalized across the data set. In other words, the slope for each value is divided by the maximum slope found for any value, and the linearity for each value is divided by the maximum linearity found for any value. The normalized position is, for example, calculated as the difference between the maximum x position of any value and the position of the value divided by the difference between the maximum x position of any value and the minimum x position of any value.

A weighted sum of the normalized slope, the normalized linearity, and the normalized position are calculated for bcCt values 810-860. A weighted sum can also be calculated for a group of two or more bcCt values. The weighted sum is calculated according to the following equation, for example:

$W2*$(Normalized Slope)$+W1*$(Normalized Linearity)$+(1-W1-W2)*$Normalized Position)

W2 and W1 are chosen, for example, to heavily weight slope, moderately weight linearity, and lightly weight position. Heavily weighting the slope and moderately weighting the linearity is designed to capture the rising phase of a sigmoid function while avoiding the early and late plateau regions and the curved portions. Lightly weighting the position is designed to capture a rising phase of the sigmoid function at a lower x value if there are multiple rising phases.

Based on the calculated weighted sum, bcCt values 810-860 are placed in rank order. A linear range is found by attempting to extend a line from the bcCt value of highest rank. Starting with the bcCt value of highest rank, adjacent bcCt values are evaluated by computing the angle sub tended by the new candidate point and the closest two points of the linear range, for example. If the sub tended angle is within a threshold value close to 180°, then the linear range is extended in that direction. If the sub tended angle is not within a threshold value close to 180°, then the end of the linear range in that direction is found.

A distinguishing characteristic of a proximity binding assay is that, in general, log-linear segments of dilution series curves for samples with different amounts of the target protein are not parallel.

FIG. 6 shows an example of this for target protein OCT3/4 protein in the NTERA-2 cells. The per-cell protein content is known to decrease with time as the cells differentiate into neurons in response to incubation with trans-retinoic acid. If the generation of ligation product (LP) were only dependent on the starting quantity of the target protein, the log-linear regions of these curves would be parallel.

A mathematical description of the proximity binding assay must account for two processes: 1) The formation of LP and 2) the PCR amplification of LP. The governing equation for TaqMan™ monitored PCR is given by:

$$F_{C_T} = f c_{init,LP} (1+E_{LP})^{C_T} \quad (1)$$

$F_{C_T}$ fluorescence at cycle $C_T$ f: conversion factor from concentration to fluorescence $c_{init,LP}$: initial concentration of ligation product prior to PCR $E_{LP}$: PCR efficiency of the ligation product The simplest model for LP generation that can account for the non-parallel characteristic of the log-linear regions is an exponential model:

$$C_{LP} = (\rho_{pc} N_c)^{\beta_{pc}} + B_{CLP} \quad (2)$$

$C_{LP}$: concentration of ligation product $B_{CLP}$: spontaneous concentration of ligation product generated in antibody reagent devoid of protein $\rho_{pc}$: protein content of protein p per cell of cell type c, the PQD factor (Protein Quantity Dependence)

$N_c$: cell concentration for cell type c $\beta_{pc}$: effects of protein p and/or other cellular material on LP generation for cell type c that result in acceleration or deceleration of LP generation with target protein and cell concentration, the SCD factor (Sample Concentration Dependence)

Combining equations 1 and 2 yields the following formula, the EM fold change:

$$\frac{\rho_{p,c2}}{\rho_{p,c1}} = b^{(\hat{B}_{c2} + C_{Ts2}|_{N_{c2}=0} - \hat{B}_{LPs2})/\hat{A}_{c2} - (\hat{B}_{c1} + C_{Ts1}|_{N_{c2}=0} - \hat{B}_{LPs1})/\hat{A}_{c1}} \quad (3)$$

$\rho_{p,c}$: protein content of protein type p per cell for cell type c b: base of the logarithm used $\hat{A}_c, \hat{B}_c$: slope and intercept of the linear regression of $\Delta C_T$ vs. $\log_b N_c$ where $\Delta C_T$ is $C_T|_{N_c=0} - C_T$ and $N_c$ is the concentration of cell type c $C_{Ts}|_{N_c=x}$: $C_T$ value on system s (includes instrument, plate, reagents, and run) when cell concentration of cell c is x $\hat{B}_{LPs}$: intercept of the linear regression of $C_T$ vs. $\log_b C_{LP}$ on system s where $C_{LP}$ is the concentration of ligation product This formulation assumes that 1) LP is the same molecule for all protein targets, 2) there is a log-linear region in the dilution curves, and 3) cellular debris has no influence on the PCR of LP. All quantities of equation 3 can be derived from data obtained from normal application of the proximity binding assay to unknown and reference samples except for the pure LP intercepts:

$$\hat{B}_{LPs1} \quad (4)$$

and $$\hat{B}_{LPs2}, \quad (5)$$

which are the γ intercepts for the pure LP $C_T$ vs. log(LP concentration) curves on systems 1 and 2.

According to various embodiments of methods for the analysis of PBA data, as indicated in step 140 of method 100 of FIG. 1, log-linear regression lines are calculated for all linear ranges of bcCt values versus input quantity. The linear regression lines are calculated to determine the slope and γ intercept values for bcCt values versus input quantity used in equation 3.

According to various embodiments of methods for the analysis of PBA data, as indicated in step 150 of method 100 of FIG. 1, a calibration method is performed to estimate values for the pure LP intercepts.

According to various embodiments of methods for the analysis of PBA data, a direct approach can be used to estimate the pure LP intercepts. In this direct approach, linear regression lines are calculated from data collected from a dilution series of LP made from a standard solution of LP. This requires developing and adding the standard solution of LP to the proximity binding assay. Alternatively, a dilution series of LP is not needed if it is known that the LP concentration of the standard solution is 1 or it is assumed that the slope of the LP dilution series Ct versus LP concentration curve is known (approximately −3.32 for 100% PCR efficiency). In all these cases, they intercept values for log-linear regression lines of Ct values versus concentration of ligation product is determined as the Ct value at the ligation product concentration of 1.

According to various embodiments of methods for the analysis of PBA data, as indicated in step 160 of method 100 of FIG. 1, a quantitative result is calculated using the EM fold change of equation 3 after it has been calibrated using calibration samples. Using the direct calibration method described above, the values for variables 4 and 5 are calculated directly. A relative target protein quantity is then calculated for two cell types using equation 3, the EM fold change. An absolute quantity is calculated if the absolute quantity of the reference sample is known.

According to various embodiments of methods for the analysis of PBA data, an indirect approach can also be used to estimate the variables of the EM fold change. An indirect approach can provide an estimate using the proximity binding assay as described if there are a pair of calibration samples for which the relative protein quantity is a known value, f, and the log-linear regions of the pair are not parallel. If it is assumed that all concentration-independent variability between samples other than that caused by differences in target protein quantity can be accounted for by the $C_T$ values at zero cell input, i.e., a constant offset accounts for this variability, since variables (4) and (5) are simply constant offsets for the LP dilution series, it follows that $$EM_{th} = \hat{B}_{LPs2} - C_{Ts2}|_{N_{c2}=0} = \hat{B}_{LPs1} - C_{Ts1}|_{N_{c2}=0} \quad (6)$$

Combining equation 3 and 6 and solving for the EM threshold parameter of equation 6 produces:

$$EM_{th} = \frac{1}{1/\hat{A}_{c2} - 1/\hat{A}_{c1}} \left( \frac{\hat{B}_{c2}}{\hat{A}_{c2}} - \frac{\hat{B}_{c1}}{\hat{A}_{c1}} - \log f \right) \quad (7)$$

If there are a pair of calibration samples for which the relative protein quantity is known, then the EM threshold, $EM_{th}$, can be calculated using equation 7. In turn, the EM threshold can be used to find the relative quantity for any pair of reference and test samples. Substituting the relationships in equations 6 and 7 back into equation 3 yields the following formula for relative target protein quantity parameterized by the EM threshold:

$$\frac{\rho_{p,s2}}{\rho_{p,s1}} = b^{[(\hat{B}_{s2} - EM_{th})/\hat{A}_{s2} - (\hat{B}_{s1} - EM_{th})/\hat{A}_{s1}]} \quad (8)$$

Where:
$\rho_{p,s}$=concentration of protein, p, within sample s
s1, s2 is the reference and test sample, respectively
$\hat{B}_s$ is the intercept of the regression line for samples in the bcCt vs. $\log_b$ (Input Quantity) curve.
$\hat{A}_s$ is the slope of the regression line for samples in the bcCt vs. $\log_b$ (Input Quantity) curve.
b=base of the logarithm
c1, c2 is the calibrator sample 1 and 2, respectively
$Ct_{NPC}$=Ct value of the No Protein Control
f=the known fold difference of calibrator sample 2 relative to calibrator sample 1
$EM_{th}$=the EM threshold parameter According to various embodiments of methods for the analysis of PBA data, as indicated in step 160 of method 100 of FIG. 1, an estimate of absolute or relative protein quantity is calculated using the theoretical model of equation 8, for example, after the indirect calibration method, described above, is used to determine the value for the EM threshold of equation 7, for example.

According to various embodiments of methods for the analysis of PBA data, as indicated in step 170 of method 100 of FIG. 1, a confidence interval is estimated for the result found in step 160. The result found in step 160 is calculated, for example, using equation 3 or equation 8. A number of other assumptions are also made. The calibration samples used in conjunction with equation 3 or equation 8 are assumed to be statistically independent of the reference and test samples for which a quantitative result is sought. A confidence interval is found by assuming that estimates of the parameters of equation 3 or 8 are normally distributed. It is assumed that input data are normally distributed about the linear regression lines with the same variability for all dilutions.

The data points of a dilution series are notated as:

$(x_i, y_i): i \in [1, N]$ $x: \log_b(\text{input quantity})$ $y: bcCt \quad (9)$ The following estimates are then made $$\bar{x} = \frac{1}{N} \sum_1^N x_i \quad (10)$$

$$\bar{y} = \frac{1}{N} \sum_1^N y_i$$

$$\hat{A} = \frac{\sum (x_i - \bar{x})(y_i - \bar{y})}{\sum (x_i - \bar{x})^2}$$

-continued $$\hat{B} = \bar{y} - \hat{A}\bar{x}$$

$$\hat{\sigma}^2 = \frac{1}{N-2}\sum(y_i - \hat{B} - \hat{A}x_i)^2$$

and the $(1-\alpha)$ confidence band, $C_\alpha$ about the regression line is given by $$C_\alpha(x) = \hat{A}x + \hat{B} \pm \tilde{t}_{N-2,1-\alpha/2}\hat{\sigma}\sqrt{\frac{1}{N} + \frac{(x-\bar{x})^2}{\sum(x_i-\bar{x})^2}} \quad (11)$$

$$\tilde{t}_{N-2,1-\alpha/2} \ni \int_{-\infty}^{\tilde{t}_{N-2,1-\alpha/2}} t_{N-2} = 1 - \alpha/2 \quad (12)$$

where $t_{N-2}$ is the t-distribution with $N-2$ degrees of freedom. Equations 11 and 12 can be rewritten as $$C_\alpha(x) \equiv \hat{A}x + \hat{B} \pm \hat{\tau}\sqrt{S + (x-\bar{x})^2} \quad (13)$$

$$S \equiv \frac{1}{N}\sum(x_i - \bar{x})^2$$

$$\hat{\tau} \equiv \tilde{t}_{N-2,1-\alpha/2}\hat{\sigma}\sqrt{\frac{1}{\sum(x_i-\bar{x})^2}}$$

To find the confidence bounds for the absolute or relative target protein quantity between two samples, two lines are found that fall within the region defined by the two boundaries of equation 13 and the confidence interval for the EM threshold that maximize and minimize the following quantity:

$$(\hat{B} - EM_{th})/\hat{A} \quad (14)$$

Figure 9:
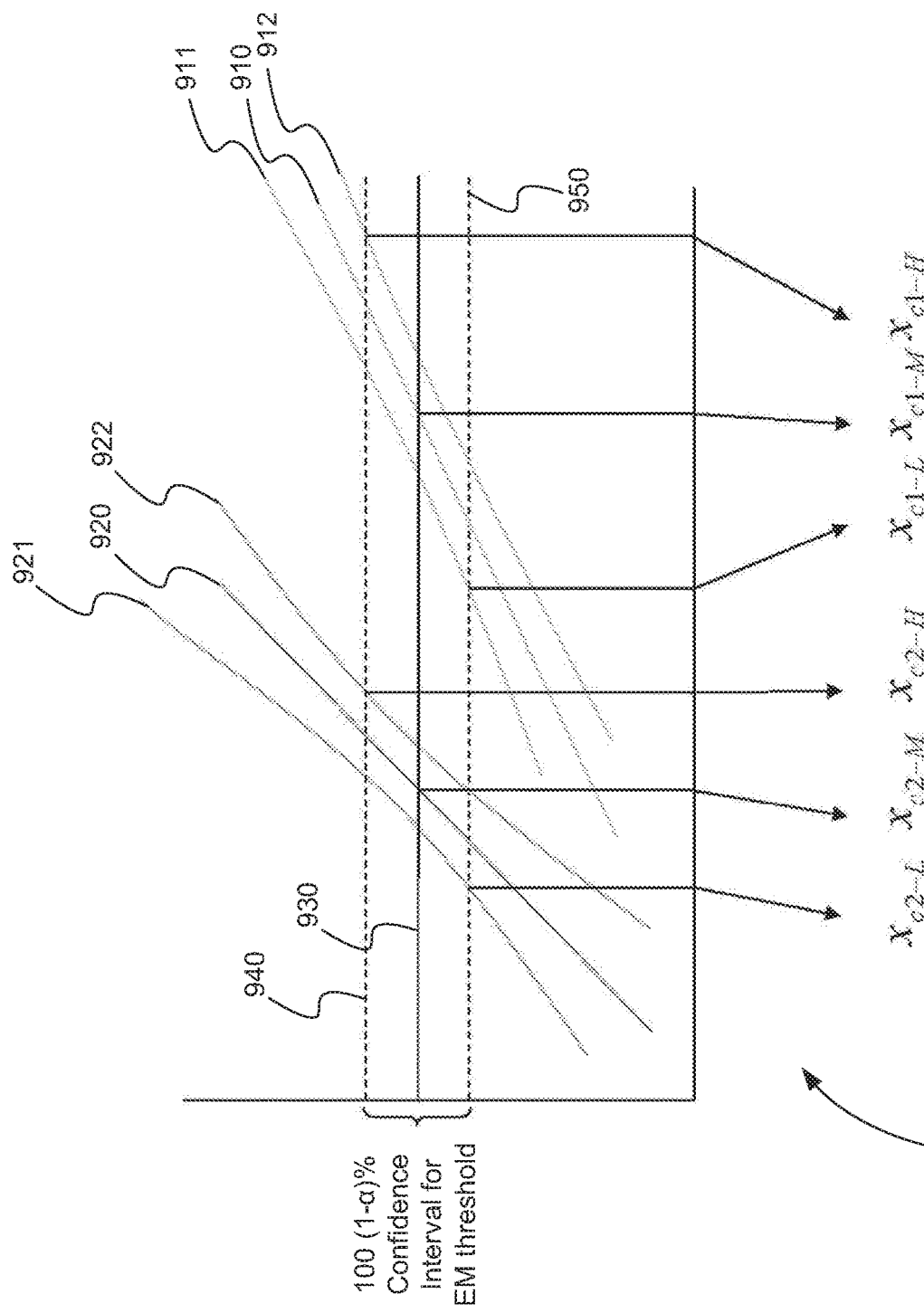
FIG. 9 depicts the intersection of exemplary regression lines of two samples with background corrected Ct values according to various embodiments for calculating confidence intervals.

Regression lines 910 for a first sample and regression lines 920 for a second sample are shown plotted in plot 900 of FIG. 9. Their respective confidence interval boundaries are 911 and 912 for the first sample and 921 and 922 for the second sample. The EM threshold is shown as the horizontal line 930 and its confidence interval as line 940 and line 950. FIG. 1 illustrates which pair of points to pick to minimize or maximize equation 14 while remaining within the confidence regions for sample 1, sample 2, and the EM threshold. For example, in the figure $$x_{c2-M} < x_{c1-M} \quad (15)$$

In this case, the best estimate of the relative target protein quantity and the confidence interval around it is given by the triplet of equation 16:

$$b^{x_{c1-L}-x_{c2-H}}, b^{x_{c1-M}-x_{c2-M}}, b^{x_{c1-H}-x_{c2-L}} \quad (16)$$

Figure 10:
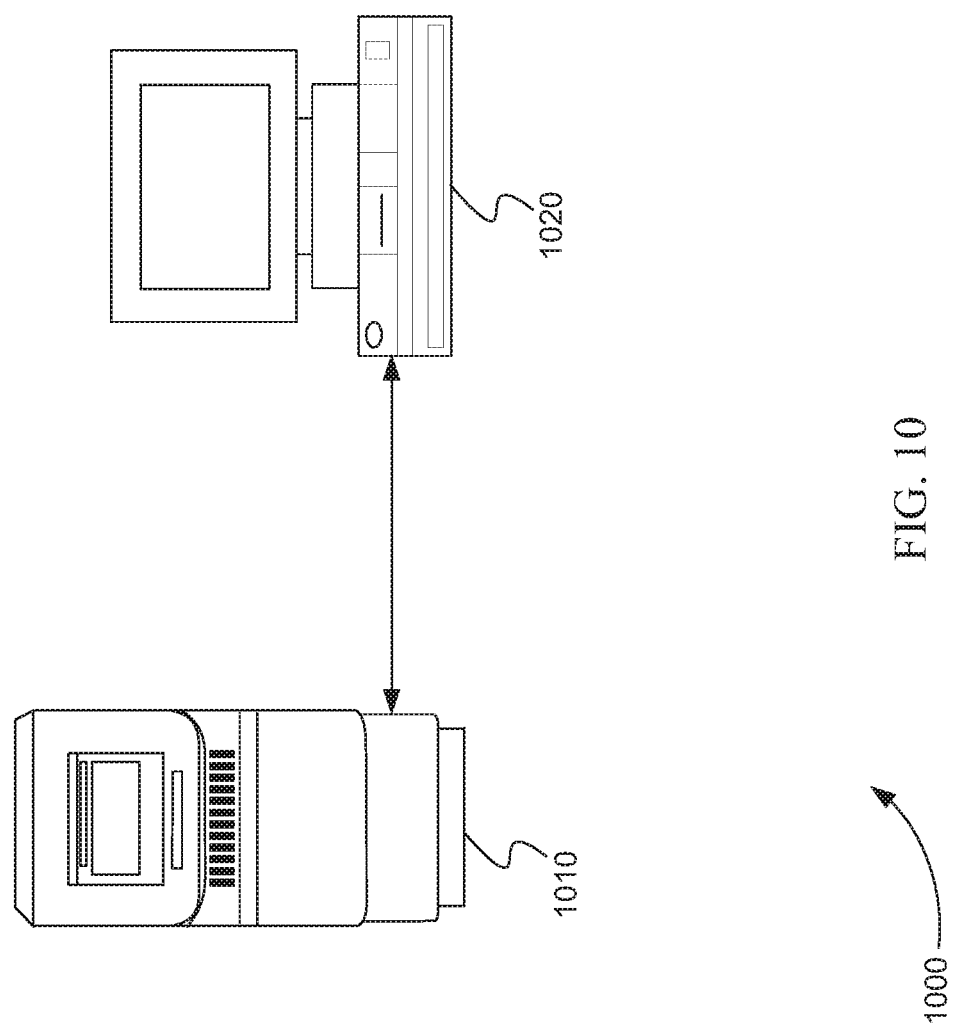
FIG. 10 depicts an exemplary system for analyzing PBA data according to various embodiments.

If $$x_{c2-M} > x_{c1-M} \quad (17)$$

the best estimate of the relative target protein quantity and the confidence interval around it is given by the triplet of equation 18:

$$b^{x_{c1-H}-x_{c2-L}}, b^{x_{c1-M}-x_{c2-M}}, b^{x_{c1-L}-x_{c2-H}} \quad (18)$$

$$x_{c-M} = \frac{EM_{th} - \hat{B}}{\hat{A}} \quad (19)$$

$$x_{c2-L}, x_{c2-H}, x_{c1-L}, \text{ and } x_{c1-H} \quad (20)$$

are obtained by solving the following quadratic equation as appropriate for the first sample, the second sample, and parameter $T_h$ as indicated $$(\hat{A}^2 - \hat{\tau})x^2 - 2(\hat{A}(T_h - \hat{B}) - \bar{x}\hat{\tau}^2)x + (\hat{B} - T_h)^2 - (S + \bar{x}^2)\hat{\tau}^2 = 0 \quad (21)$$

for $x_{c1-L}$ and $x_{c2-L}$ use the lower root with $T_h = EM_{th,lwr}$
for $x_{c1-H}$ and $x_{c2-H}$ use the upper root with $T_h = EM_{th,upr}$ FIG. 10 shows a system 1000 for analyzing PBA data, in accordance with various embodiments. System 1000 includes thermal cycler instrument 1010 and computing system 1020. Thermal cycler instrument 1010 and computing system 1020 may each comprise the exemplary computing system illustrated in FIG. 4, in various embodiments. In some embodiments, thermal cycler instrument 1010 may include a processor to perform the methods according to various embodiments described herein. Thermal cycler instrument 1010 performs a proximity binding assay on at least one test sample, at least one reference sample, a background sample, and one or more calibration samples. Thermal cycler instrument 1010 generates at least one set of test sample data, at least one set of reference sample data, a background sample data set, and one or more sets of calibration sample data.

Computing system 1020 is in communication with thermal cycler instrument 1010 in some embodiments. Computing system 1020 receives from thermal cycler instrument 1010 the at least one set of test sample data, the at least one set of reference sample data, the background sample data set, and the one or more sets of calibration sample data. Computing system 1020 determines Ct values for the at least one set of test sample data and the at least one set of reference sample data. Computing system 1020 calculates background corrected Ct values for each value in the test sample data set and the reference sample data set using a corresponding value in a background sample data set. Computing system 1020 determines a linear range for the background corrected Ct values as a function of sample quantity for each set of test sample data and reference sample data. Computing system 1020 calculates a linear regression line for each linear range that is determined. Computing system 1020 estimates one or more parameter values of an exponential model (EM) fold change formula from the one or more sets of calibration sample data. Finally, computing system 1020 calculates a target protein quantity and a confidence interval for this quantity using the linear regression lines calculated for the test sample data and the reference sample data and the one or more estimated parameter values of the EM fold change formula estimated from the one or more sets of calibration sample data.

In various embodiments, computing system 1020 further detects and removes outlier Ct values before determining a linear range for the background corrected Ct values. Computing system 1020 detects outlier Ct values by determining if a background corrected Ct value deviates from its replicate group median by more than a number of dilution-series standard deviations. In various embodiments, the standard deviation is calculated based on a majority of background corrected Ct values in a replicate group above or below a threshold. A minority of background corrected Ct values in the replicate group are considered outliers if the minority of background corrected Ct values differ from the median of the majority of background corrected Ct values by more than a specified number of standard deviations.

In various embodiments, computing system 1020 determines the linear range for the background corrected Ct values by performing three steps. In step 1, a weighted sum of the normalized slope, the normalized linearity, and the normalized position is calculated each of a plurality of the background corrected Ct values. In step 2, the plurality of the background corrected Ct values are ranked based on the calculated weighted sum. In step 3, a linear range is extended in two directions from a background corrected Ct value with the highest ranked weighted sum until a threshold is reached in each direction.

In various embodiments, the one or more sets of calibration sample data are generated from a standard solution of ligation product (LP). The one or more parameter values estimated for the EM fold change formula include one or more pure LP intercepts.

Alternatively, in various embodiments, the one or more sets of calibration sample data are generated from at least a pair of calibration samples for which the relative protein quantity is known. The one or more parameter values estimated for the EM fold change formula include an EM threshold.

In various embodiments, computing system 1020 further calculates a confidence interval for the target protein quantity.

As mentioned above, the steps performed by computing system 1020 may be performed, in various embodiments, by computing system 500 (FIG. 4) included in thermal cycler instrument 1010.

Figure 11:
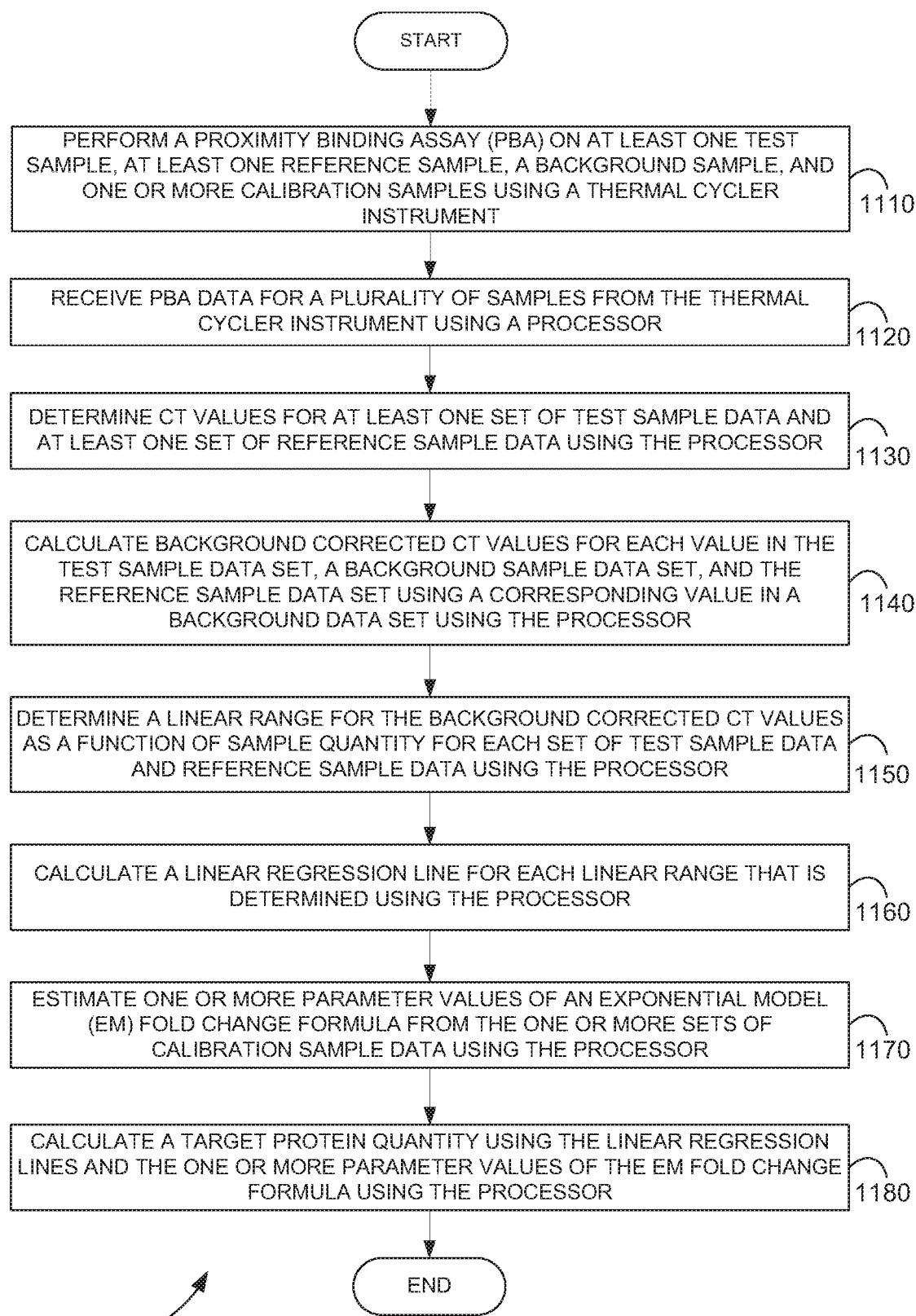
FIG. 11 depicts a flowchart showing a method for analyzing PBA data according to various embodiments.

FIG. 11 depicts a flowchart showing a method 1100 for analyzing PBA data, in accordance with various embodiments.

In step 1110 of method 1100, a proximity binding assay is performed on at least one test sample, at least one reference sample, at least one background sample, and at least one calibration sample using a thermal cycler instrument. At least one set of test sample data set, reference sample data set, background sample data set, and calibration sample data set are generated using a thermal cycler instrument.

In step 1120, PBA data is received for a plurality of samples from the thermal cycler instrument using processor 504 (FIG. 4). The PBA data includes the at least one set of test sample data, the at least one set of reference sample data, the background sample data set, and the one or more sets of calibration sample data, for example.

In step 1130, Ct values are determined for the at least one set of test sample data, the at least one set of reference sample data, and the at least one set of calibration data using processor 504.

In step 1140, background corrected Ct values are calculated for each value in the test sample data set, the reference sample data set using a corresponding value in a background sample data set using processor 504. Background corrected Ct values are calculated for each value in the calibration sample data set using a corresponding value in a background sample data set using processor 504 if the indirect approach is used for calibration.

In step 1150, a linear range is determined for the background corrected Ct values as a function of sample quantity for each set of test sample data and reference sample data using processor 504. A linear range is determined for the background corrected Ct values as a function of sample quantity for each set of calibration sample data using processor 504 if the indirect approach is used for calibration.

In step 1160, a linear regression line is calculated for each linear range that is determined using processor 504.

In step 1170, one or more parameter values of an exponential model (EM) fold change formula are estimated from the one or more sets of calibration sample data using processor 504.

In step 1180, a target protein quantity is calculated using the linear regression lines calculated for the test sample data and the reference sample data and the one or more parameter values of the EM fold change formula estimated from the one or more sets of calibration sample data using processor 504.

In various embodiments, a computer program product includes a non-transitory and tangible computer-readable storage medium encoded with a program with instructions being executed on a processor so as to perform a method for analyzing PBA data. This method may be performed by a system that may include one or more distinct software modules in some embodiments.

Figure 12:
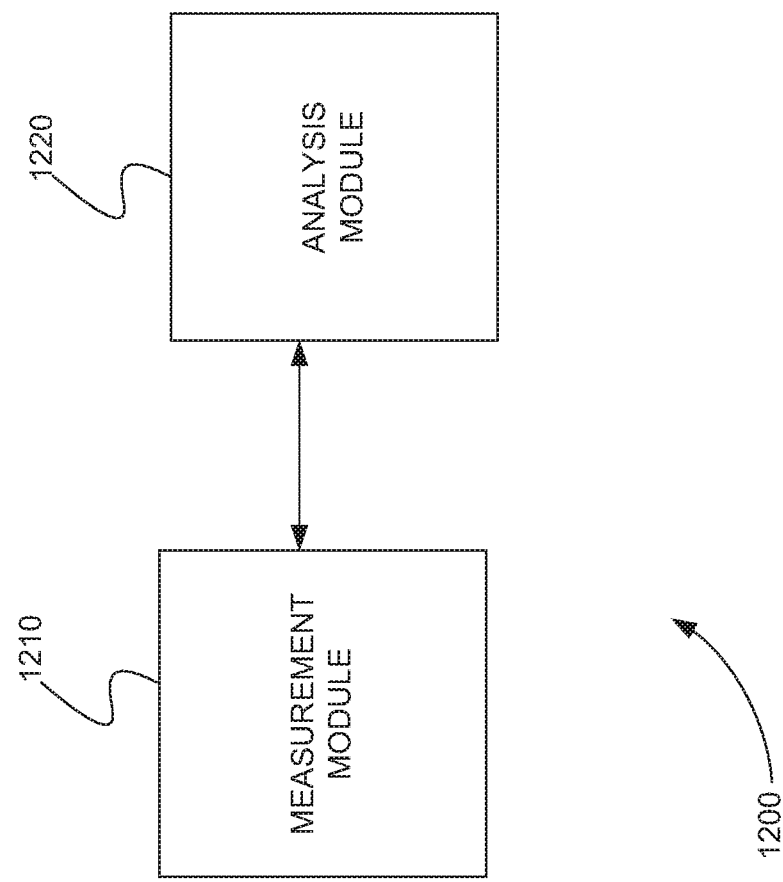
FIG. 12 depicts a system of software modules for performing a method for analyzing PBA data according to various embodiments.

FIG. 12 shows a system 1200 distinct software modules for analyzing PBA data, in accordance with various embodiments. System 1200 includes measurement module 1210 and analysis module 1220. Measurement module 1210 receives PBA data for a plurality of samples from a thermal cycler instrument. The PBA data includes at least one set of test sample data, at least one set of reference sample data, at least one background sample data point, and at least one set of calibration sample data.

Analysis module 1220 determines cycle threshold (Ct) values for the at least one set of test sample data and the at least one set of reference sample data. Analysis module 1220 calculates background corrected Ct values for each value in the test sample data set and the reference sample data set using a corresponding value in a background sample data set. Analysis module 1220 determines a linear range for the background corrected Ct values as a function of sample quantity for each set of test sample data, and reference sample data. Analysis module 1220 calculates a linear regression line for each linear range that is determined. Analysis module 1220 estimates one or more parameter values of an exponential model (EM) fold change formula from the one or more sets of calibration sample data. Analysis module 1220 calculates a target protein quantity using the linear regression lines calculated for the test sample data and the reference sample data and the one or more parameter values of the EM fold change formula for which parameter values have been estimated from the one or more sets of calibration sample data.

EXAMPLES

One method of calibration requires two or more samples for which the relative amount of target protein between the samples is known. In the absence of such samples, an example method to construct an approximation of such samples is to mix samples that are positive and negative for the target protein to form various ratios. For example, for a stem cell protein such as Lin28, Ntera2 cells, known to contain Lin28, can be mixed with Raji cells, known to be devoid of Lin28.

If the known samples are created by construction, multiple known samples can be generated with known relative target protein quantities. An estimate for the EM threshold can be generated from each possible pair of known samples. An "optimal" EM threshold can be determined by taking, for example, the mean of these estimates. Other alternatives can be, for example, the median, a trimmed mean (after excluding highest and lowest values), a trimmed median, etc.

Figure 13A:
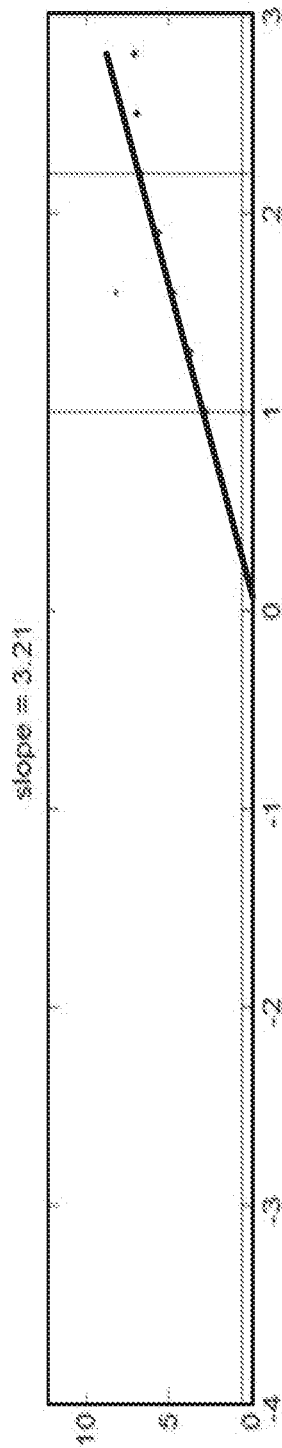
FIGS. 13A-13D illustrate a method for determining a linear range for the background corrected Ct values of a method for analyzing PBA data, according to various embodiments.
Figure 13B:
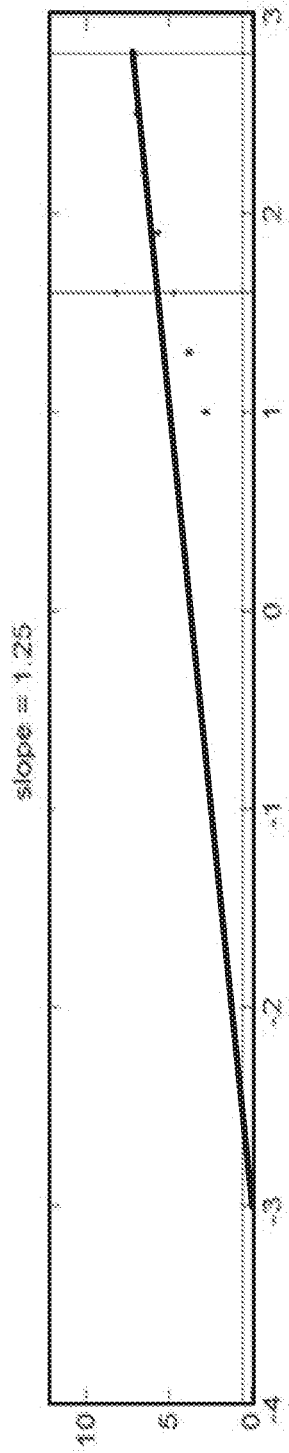
Figure 13C:
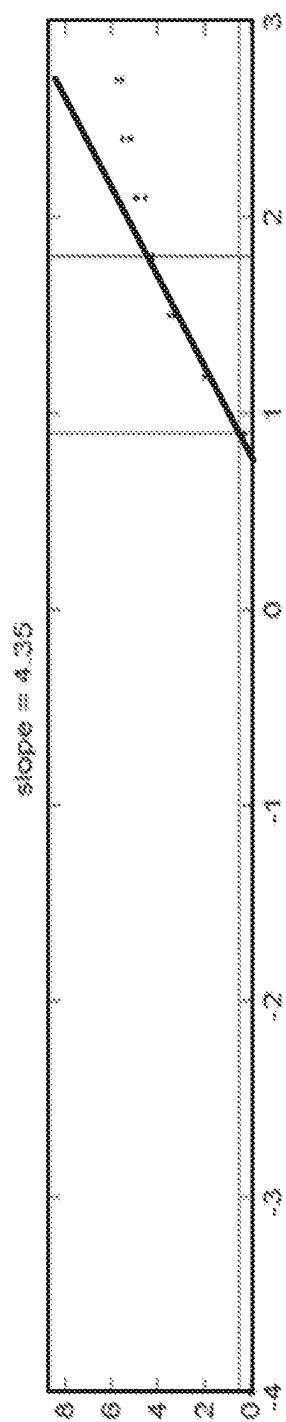
Figure 13D:
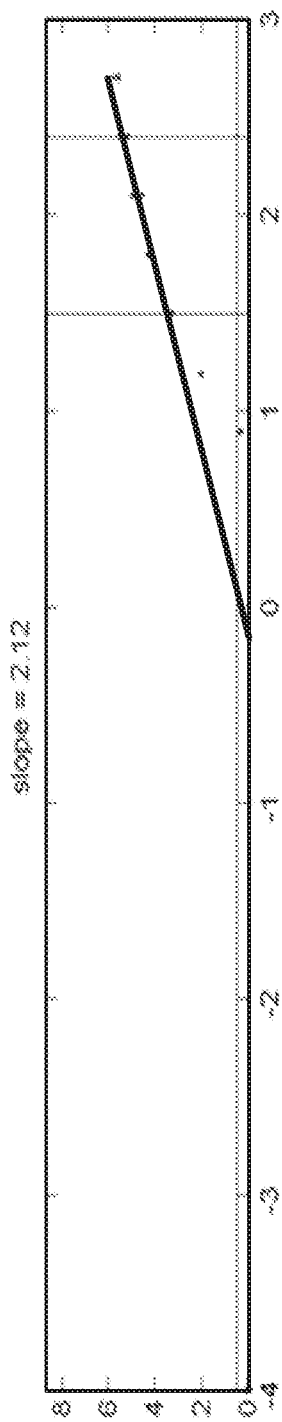

FIGS. 13A-13D illustrate a method for determining a linear range for the background corrected Ct values of a method for analyzing PBA data, according to various embodiments. The results of a previous method, described in WO 2011/017567, entitled "Methods for the Analysis of Proximity Binding Assay Data," filed on Aug. 5, 2010 and incorporated herein by reference, for determining a linear range are compared to the results of the method described herein. FIGS. 13A & 13C show the results obtained from the method described herein. FIGS. 13B & 13D show the results obtained from the previous method. In FIGS. 13A-13D the linear range is shown as the portion of the line between the two vertical lines. The method described herein can be used to capture early linear region that is part of the transition from the baseline level to the plateau portion of the sigmoid dilution series curve.

Table 1 shows improved performance between the fold change estimation between the previous method and the method described herein based on a theoretical model. For example, the previous method (described in WO 2011/017567) bases a threshold parameter, the quantification threshold (QT), on noise levels and recommends setting it to 2. The present method based on the theoretical model suggests a means to determine QT by performing calibration experiments.

TABLE 1

Percent deviations from expected fold change.
Key: average (minimum, maximum, standard deviation).
(Statistics are computed over all possible pairs of four known mixtures of Ntera2 and Raji cells (100%, 50%, 25%, 10% Ntera2. One pair is used for calibration; i.e., obtaining the QT value. The remaining pair is used for testing; i.e., estimating fold change and comparing to expected values. The three listed proteins are present only in Ntera2 cells.)

|  | Lin28 | Oct3/4 | Sox2 |
| --- | --- | --- | --- |
| Using QT = 2 | 59% (20%, 117%, 37%) | −25% (−86%, 57%, 65%) | 17% (−6%, 39%, 15%) |
| Calibrated QT* | 4.73 | 0.86 | 2.21 |
| Calibrated QT results | 7% (−4%, 11%, 7%) | 6% (−48%, 73%, 50%) | 0% (−15%, 19%, 12%) |

*Calibrated QT is the average of calibration results over each possible pair of known mixtures of Ntera2 and Raji cells after throwing out the high and low calibration values.

While the principles of this invention have been described in connection with specific embodiments, it should be understood clearly that these descriptions are made only by way of example and are not intended to limit the scope of the invention. What has been disclosed herein has been provided for the purposes of illustration and description. It is not intended to be exhaustive or to limit what is disclosed to the precise forms described. Many modifications and variations will be apparent to the practitioner skilled in the art. What is disclosed was chosen and described in order to best explain the principles and practical application of the disclosed embodiments of the art described, thereby enabling others skilled in the art to understand the various embodiments and various modifications that are suited to the particular use contemplated. It is intended that the scope of what is disclosed be defined by the following claims and their equivalence.

What is claimed is:

1. A method for analyzing proximity binding assay data to detect a target protein in a test sample having an unknown quantity of the target protein, comprising:
    conducting a proximity binding assay on the test sample, a reference sample, a background sample lacking the target protein, and at least two calibration samples having different respective known quantities of the target protein;
    generating, from the conducting, proximity binding assay data comprising at least one set of test sample data, at least one set of reference sample data, at least one background sample data set, and at least two sets of calibration sample data,
    wherein conducting the proximity binding assay comprises:
        introducing a first biorecognition probe modified with a first oligonucleotide sequence and a second biorecognition probe modified with a second oligonucleotide sequence to each of a first sample region comprising the test sample, a second sample region comprising a reference sample, and a third sample region comprising a background sample, wherein the first and second biorecognition probes are designed to specifically bind to the target protein, and the first oligonucleotide sequence and the second oligonucleotide sequence are designed to readily bind to each other when in proximity to each other, thereby generating a target nucleic acid sequence for amplification;
        obtaining, from the first sample region, the second sample region, and the third sample region, any targets for amplification resulting from introducing;
        respectively combining any targets for amplification obtained from the first sample region, the second sample region, and the third sample region with labeling probes;
        conducting an amplification reaction on respective combinations comprising the targets for amplification and the labeling probes; and
        detecting the labeling probes resulting from the amplification reaction;
    receiving, by a processor, the at least one set of test sample data, the at least one set of reference sample data, the at least one background sample data set, and the at least two sets of calibration sample data;
    determining, by the processor, cycle threshold (Ct) values for the at least one set of test sample data and the at least one set of reference sample data;
    calculating, by the processor, background corrected Ct values for each value in the at least one set of test sample data and the at least one set of reference sample data using a corresponding value in the at least one background sample data set;
    determining, by the processor, a linear range for the background corrected Ct values as a function of sample quantity;
    calculating, by the processor, a linear regression line for each linear range that is determined;
    estimating, by the processor, one or more parameter values of an exponential model (EM) fold change formula by using the at least two sets of calibration data generated from the at least two calibration samples; and
    calculating, by the processor, a quantity of the target protein in the test sample and an associated confidence interval using the linear regression lines calculated for the at least one set of test sample data and the at least one set of reference sample data and the EM fold change formula with the one or more parameter values estimated from the at least two sets of calibration sample data.

2. The method of claim 1, further comprising detecting and removing, by the processor, outlier Ct values before determining the linear range for the background corrected Ct values.

3. The method of claim 2, wherein detecting outlier Ct values comprises determining if a background corrected Ct value deviates from its replicate group median by more than a number of replicate-group standard deviations, wherein a replicate-group standard deviation is an average or median value across replicate groups of a dilution series.

4. The method of claim 3, wherein a standard deviation is calculated based on a majority of background corrected Ct values in a replicate group above or below a threshold and a minority of background corrected Ct values in the replicate group are considered outliers if the minority of background corrected Ct values differ from a median of the majority of background corrected Ct values by more than the number of replicate-group standard deviations.

5. The method of claim 1, wherein determining the linear range for the background corrected Ct values comprises calculating a weighted sum of a normalized slope, a normalized linearity, and a normalized position for a plurality of the background corrected Ct values, ranking the plurality of the background corrected Ct values based on the calculated weighted sum, and extending a linear range in two directions from a background corrected Ct value with a highest ranked weighted sum until a threshold is reached in each of the two directions.

6. The method of claim 1, wherein the at least two sets of calibration sample data is generated from a standard solution of ligation product (LP) and wherein the one or more parameter values estimated for the EM fold change formula comprise one or more pure LP intercepts.

7. The method of claim 1, wherein the one or more parameter values estimated for the EM fold change formula comprise one or more EM thresholds.

* * * * *